United States Patent
Qi et al.

(10) Patent No.: US 12,287,319 B2
(45) Date of Patent: *Apr. 29, 2025

(54) METHODS AND SYSTEMS FOR DETERMINING PLATELET CONCENTRATION

(71) Applicant: SHENZHEN MINDRAY BIO-MEDICAL ELECTRONICS CO., LTD., Shenzhen (CN)

(72) Inventors: Huan Qi, Shenzhen (CN); Bo Ye, Shenzhen (CN); Wenbo Zheng, Shenzhen (CN); Changsong Hu, Shenzhen (CN); Qi Yu, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/536,047

(22) Filed: Dec. 11, 2023

(65) Prior Publication Data

US 2024/0133864 A1    Apr. 25, 2024
US 2024/0230621 A9    Jul. 11, 2024

Related U.S. Application Data

(63) Continuation of application No. 17/075,603, filed on Oct. 20, 2020, now Pat. No. 11,841,358, which is a continuation of application No. PCT/CN2019/084687, filed on Apr. 26, 2019.

(30) Foreign Application Priority Data

Apr. 28, 2018   (WO) ................ PCT/CN2018/085197

(51) Int. Cl.
| | | |
|---|---|---|
| *G01N 33/49* | (2006.01) | |
| *G01N 15/06* | (2006.01) | |
| *G01N 33/487* | (2006.01) | |
| *G16H 10/40* | (2018.01) | |
| *G16H 15/00* | (2018.01) | |
| *G16H 40/67* | (2018.01) | |
| *G01N 15/01* | (2024.01) | |
| *G01N 15/075* | (2024.01) | |

(52) U.S. Cl.
CPC ......... *G01N 33/49* (2013.01); *G01N 15/0656* (2013.01); *G01N 33/48707* (2013.01); *G16H 10/40* (2018.01); *G16H 15/00* (2018.01); *G16H 40/67* (2018.01); *G01N 2015/018* (2024.01); *G01N 15/075* (2024.01)

(58) Field of Classification Search
CPC ...................................................... G01N 33/49
See application file for complete search history.

(56) References Cited

U.S. PATENT DOCUMENTS

| | | | |
|---|---|---|---|
| 5,616,501 | A | 4/1997 | Rodriguez et al. |
| 6,525,807 | B1 | 2/2003 | Morikawa et al. |
| 11,841,358 | B2 * | 12/2023 | Qi ..................... G01N 15/12 |
| 2006/0160229 | A1 | 7/2006 | Lopez et al. |
| 2007/0105230 | A1 | 5/2007 | Beckman |

FOREIGN PATENT DOCUMENTS

| | | |
|---|---|---|
| CN | 1549925 A | 11/2004 |
| CN | 1034 72034 A | 12/2013 |
| CN | 103471980 A | 12/2013 |
| CN | 103471982 A | 12/2013 |
| CN | 103472216 A | 12/2013 |
| CN | 103491771 A | 1/2014 |
| CN | 104541149 A | 4/2015 |
| CN | 104903699 A | 9/2015 |
| CN | 106018771 A | 10/2016 |
| EP | 3258274 A1 | 12/2017 |

OTHER PUBLICATIONS

Kunicka, J E. et al, "Improved Platelet Counting USing Two-Dimensional Laser Light Scatter, A New Approach to Platelet Counting," American Journal of Clinical Pathology, Aug. 2000, pp. 283-289, 7 pages.

(Continued)

*Primary Examiner* — Albert M Navarro
(74) *Attorney, Agent, or Firm* — BAYES PLLC

(57) ABSTRACT

Disclosed are a method for determining a platelet concentration of a blood sample, a hematology system and a storage medium. The method for determining a platelet concentration in a blood sample includes: forming a first suspension by mixing a first aliquot of the blood sample with a diluent; forming a second suspension by mixing a second aliquot of the blood sample with a lytic agent and a fluorescent dye to lyse red blood cells and stain white blood cells; measuring DC impedance signals of the first suspension passing through an aperture; measuring light scatter signals and fluorescent signals of the second suspension passing through an optical flow cell; analyzing DC impedance signals of the first suspension to obtain a first platelet distribution; analyzing light scatter signals and fluorescent signals of the second suspension to differentiate platelets from white blood cells and to obtain a second platelet distribution; and determining platelet data, such as the platelet concentration of the blood sample using the first and second platelet distributions.

21 Claims, 11 Drawing Sheets

(56) References Cited

OTHER PUBLICATIONS

Shi, Z et al, "Clinical Performance Evaluation of Low-Count Platelet Samples for Mindray BC-6800 Automatic Hematology Analyzer," China Medical Equipment, vol. 14, No. 2, Feb. 2017, pp. 23-26, 4 pages.
Li, H. et al, "Analysis on causes and countermeasures on pseudo-reduction of platelet count by blood cell analyzer," Journal of Clinical and Experimental Medicine, vol. 13, No. 9, May 2014, pp. 764-767, 4 pages.
Extended European Search Report issued in related European Application No. 24180348.5, mailed Sep. 16, 2024, 10 pages.

* cited by examiner

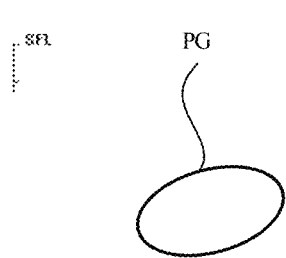
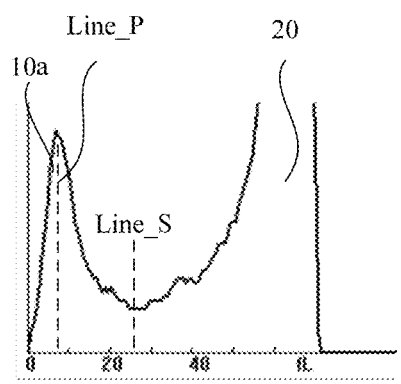
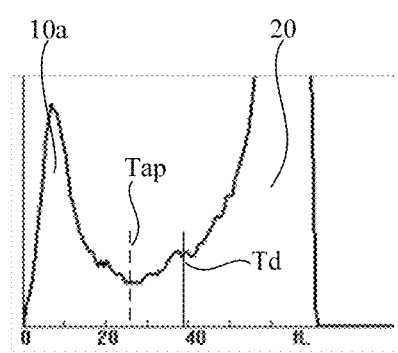
Fig. 9A Fig. 9B Fig. 9C
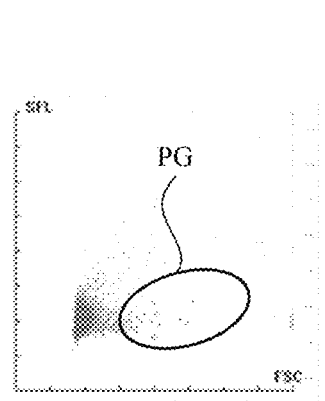
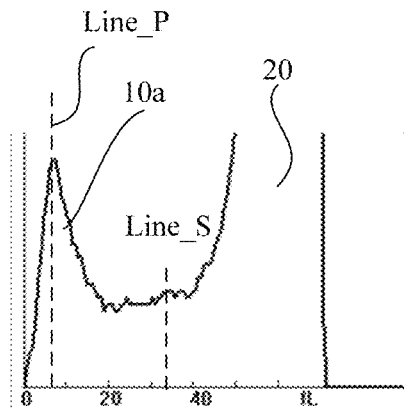
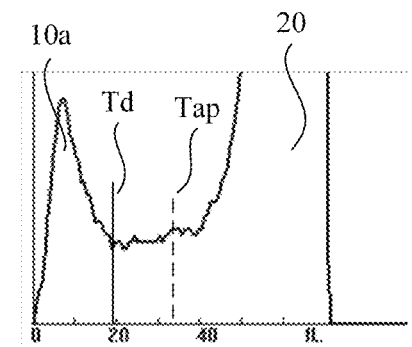
Fig. 10A Fig. 10B Fig. 10C

METHODS AND SYSTEMS FOR DETERMINING PLATELET CONCENTRATION

CROSS-REFERENCE

This application is a continuation of U.S. patent application Ser. No. 17/075,603, filed Oct. 20, 2020 for METHODS AND SYSTEMS FOR DETERMINING PLATELET CONCENTRATION which is a continuation of International Application No. PCT/CN2019/084687, filed Apr. 26, 2019, which claims benefit of priority to International Application No. PCT/CN2018/085197, filed Apr. 28, 2018. The contents of all the above application are incorporated herein by reference.

TECHNICAL FIELD

The present disclosure relates to methods and systems for determining a platelet concentration in a blood sample. More specifically, the present disclosure relates to determination of the platelet concentration using an impedance measurement of platelets in a diluted blood sample in combination with an optical measurement of platelets in a lysed blood sample.

BACKGROUND

In order to determine the course of treatment of a patient, it is generally mandated clinical practice to obtain an accurate platelet count. For example, if the platelet count is less than 20×10 9 per liter, it may become necessary to transfuse platelets. Otherwise, the patient may potentially have life threatening bleeding.

Most existing hematology analyzers count platelets using impedance measurement. Using impedance measurements of a diluted blood sample, cells can be classified as platelets and red blood cells according to their volumes. Although, in most cases, an impedance measurement system provides relatively accurate results in measuring platelet count, it has certain limitations. For example, an impedance measurement method is not able to differentiate between platelets and interfering particles, such as microcytes and schistocytes (fragmented red blood cells), which leads to falsely high platelet count. Conversely, large platelets and giant platelets may fall outside a defined threshold for platelets and be classified as red blood cells, which leads to falsely low platelet count.

With impedance measurements, typically a mathematical curve fitting is performed on the platelet volume distribution in a histogram between 2 and 20 femtoliters (fL) in order to extend a dynamic range up to 70 fL. However, an accurate platelet count cannot be obtained under certain circumstances, for example, if the platelet distribution does not fit into a logarithmic distribution, or if the upper end of the platelet distribution is not decreasing, the mean platelet volume is outside its normal range, and the fitting mode is no longer applicable. Under these circumstances, it is often that only those platelets located in the range between 2 and 20 fL are reported by the impedance measurement system with flagging.

To overcome deficiencies of impedance measurement methods, several high-end hematology analyzers have incorporated an additional optical measurement of platelets. However, although optical measurements reduce aforementioned interferences to platelet measurement, additional channel of optical measurement substantially increases complexity of the instrument, and raises the costs of instrument manufacturing and maintenance services.

Therefore, there is a need for a simple, less costly, yet reliable detection method and instrument system for accurately determining a platelet concentration in a blood sample, particularly in the presence of interference materials.

SUMMARY

In one aspect, the present disclosure is directed to a method of determining a platelet concentration in a blood sample, which includes mixing a first aliquot of the blood sample with a diluent to form a first suspension; mixing a second aliquot of the blood sample with a lytic agent and a fluorescent dye to lyse red blood cells and stain white blood cells to form a second suspension; measuring DC impedance signals of the first suspension passing through an aperture; measuring light scatter signals and fluorescent signals of the second suspension passing through an optical flow cell; analyzing the DC impedance signals of the first suspension to obtain a first platelet distribution; analyzing the light scatter signals and the fluorescent signals of the second suspension to differentiate platelets from white blood cells and to obtain a second platelet distribution; and determining the platelet concentration of the blood sample using the first and second platelet distributions. Moreover, the method further includes differentiating the white blood cells of the blood sample using the light scatter signals and the fluorescent signals of the second suspension into white blood cell subpopulations that include monocytes, lymphocytes, neutrophils and eosinophils.

In a further aspect, the present disclosure is directed to a hematology system for determining a platelet concentration in a blood sample. The hematology system includes a first module that includes a first mixing chamber configured to mix a first aliquot of the blood sample with a diluent to form a first suspension, and a DC impedance detector equipped with an aperture in a flow path connected with the first mixing chamber, the DC impedance detector configured to measure DC impedance signals of the first suspension passing through the aperture; a second module that includes a second mixing chamber configured to mix a second aliquot of the blood sample with a lytic agent and a fluorescent dye to lyse red blood cells and stain white blood cells to form a second suspension, a light source configured with a light beam aimed at an orifice of an optical flow cell in a flow path connected with the second mixing chamber, and one or more optical detectors equipped with the optical flow cell and configured to measure light scatter signals and fluorescent signals of the second suspension passing through the optical flow cell; and a data processing module operably connecting with the DC impedance detector in the first module and the one or more optical detectors in the second module, respectively, the data processing module including a processor and a non-transitory computer readable medium programmed with computer application program that, when executed by the processor, causes the processor to generate a first platelet distribution from the DC impedance signals of the first suspension, to differentiate platelets from white blood cells using the light scatter signals and the fluorescent signals of the second suspension to generate a second platelet distribution, and to determine the platelet concentration of the blood sample using the first and second platelet distributions. Moreover, the data processing module is further configured to differentiate white blood cells of the blood sample using the light scatter signals and the fluorescent signals of the second suspension into white blood cell subpopulations that include monocytes, lymphocytes, neutrophils and eosinophils.

In yet another aspect, the present disclosure is directed to a method of determining a platelet concentration in a blood sample, which includes mixing a first aliquot of the blood sample with a diluent to form a first suspension; mixing a second aliquot of the blood sample with a lytic agent to lyse red blood cells to form a second suspension; measuring DC impedance signals of the first suspension passing through an aperture; measuring forward angle light scatter signals and side scatter signals or medium angle light scatter signals of the second suspension passing through an optical flow cell; analyzing the DC impedance signals of the first suspension to obtain a first platelet distribution; analyzing the forward angle light scatter signals, and the side scatter or the medium angle light scatter signals of the second suspension to differentiate platelets from white blood cells and to obtain a second platelet distribution; and determining the platelet concentration of the blood sample using the first and second platelet distributions. Moreover, the method further includes differentiating white blood cells of the blood sample using the forward angle light scatter signals and the side scatter signals or the medium angle light scatter signals of the second suspension into white blood cell subpopulations that include monocytes, lymphocytes, neutrophils and eosinophils.

In a further aspect, the present disclosure is directed to a hematology system for determining a platelet concentration in a blood sample. The system includes a first module that includes a first mixing chamber configured to mix a first aliquot of a blood sample with a diluent to form a first suspension, and a DC impedance detector equipped with an aperture in a flow path connected with the first mixing chamber, the DC impedance detector configured to measure DC impedance signals of the first suspension passing through the aperture; a second module that includes a second mixing chamber configured to mix a second aliquot of the blood sample with a lytic agent to lyse red blood cells to form a second suspension, a light source configured with a light beam aimed at an orifice of an optical flow cell in a flow path connected with the second mixing chamber, and one or more optical detectors equipped with the optical flow cell and configured to measure forward angle light scatter signals, and side scatter or medium angle light scatter signals of the second suspension passing through the optical flow cell; a data processing module operably connecting with the DC impedance detector in the first module and the one or more optical detectors in the second module, respectively, the data processing module including a processor and a non-transitory computer readable medium programmed with computer application program that, when executed by the processor, causes the processor to generate a first platelet distribution from the DC impedance signals of the first suspension, to differentiate platelets from white blood cells using the forward angle light scatter signals and the side scatter signals or the medium angle light scatter signals of the second suspension to generate a second platelet distribution, and to determine the platelet concentration of the blood sample using the first and second platelet distributions. Moreover, the data processing module is further configured to differentiate white blood cells of the blood sample using the forward angle light scatter signals and the side scatter signals or the medium angle light scatter signals of the second suspension into white blood cell subpopulations comprising monocytes, lymphocytes, neutrophils and eosinophils.

The advantages of the present disclosure will become apparent from the following description taken in conjunction with the accompanying drawings showing exemplary embodiments.

BRIEF DESCRIPTION OF THE DRAWINGS

FIGS. 3A-3C illustrate a process of obtaining a derived platelet volume histogram $H_{Plt-L}$ from the second suspension of a blood sample according to one embodiment of the present disclosure, in which FIG. 3A is a SFL vs. FSC scattergram of the second suspension, FIG. 3B is an enlarged view of a platelet region in the SFL vs. FSC scattergram shown in FIG. 3A, and FIG. 3C is a derived platelet volume histogram $H_{Plt-L}$ of the second suspension.

FIGS. 9A-9C illustrate a process of determining a platelet concentration in a blood sample using a derived separation threshold Td in one embodiment of the present disclosure.

FIGS. 10A-10C further illustrate the process of determining a platelet concentration in a blood sample using a derived separation threshold Td.

It is noted that in the drawings like numerals or symbols refer to like components.

DETAILED DESCRIPTION

Figure 1:
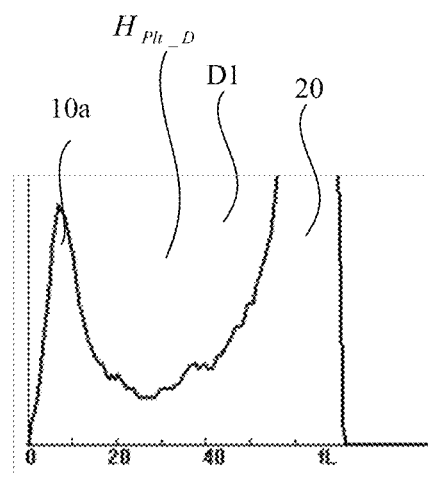
FIG. 1 shows a platelet DC impedance histogram $H_{Plt-D}$ from a first suspension of a blood sample.

The present disclosure generally relates to methods and hematology systems for determining a platelet concentration in a blood sample. Embodiments are described more fully hereinafter with reference to the accompanying drawings. The various embodiments may, however, be embodied in many different forms and should not be construed as limited to the embodiments set forth herein.

In some embodiments, the present disclosure provides a method of determination of platelet concentration using an impedance measurement of platelets in a diluted blood sample in combination with an optical measurement of platelets in a lysed blood sample. Herein, platelet concentration is also often referred to as platelet count in hematology, and is reported as number of platelets per liter of blood.

In one embodiment, the method comprises mixing a first aliquot of a blood sample with a diluent to form a first suspension, mixing a second aliquot of the blood sample with a lytic agent and a fluorescent dye to lyse red blood cells and stain white blood cells to form a second suspension, measuring DC impedance signals of the first suspension passing through an aperture, measuring light scatter and fluorescent signals of the second suspension passing through an optical flow cell, analyzing the DC impedance signals of the first suspension to obtain a first platelet distribution, analyzing light scatter and fluorescent signals of the second suspension to differentiate platelets from white blood cells and to obtain a second platelet distribution, and determining a platelet concentration of the blood sample using the first and second platelet distributions.

The first suspension is a diluted blood sample. A blood diluent is commonly used on hematology analyzers to dilute a blood sample for measuring red blood cells and platelets. The diluent typically contains one or more salts, such as alkali metal salt(s), and is adjusted to be isotonic for maintaining red blood cell volumes. Commercially available blood diluents can be used for diluting the first aliquot of the blood sample to form the first suspension, for example, M-68DS diluent and M-53D diluent produced by Shenzhen Mindray Bio-Medical Electronics Co., Ltd., Shenzhen, China.

The direct current (DC) impedance signals of the first suspension can be measured with a DC impedance detector equipped with a non-focused flow aperture or a focused flow aperture in a flow path. When a particle or a blood cell suspended in a conductive solution passes through an aperture, an electrical signal can be measured due to impedance change. The pulse shape, height and width of the impedance signals are directly correlated to the size or volume of a particle, and can be converted to the volume of the subject particle. When two or more particles of different sizes are measured, a frequency histogram obtained from the impedance measurement may represent a size distribution of these particles. Detection methods used for blood cell counting and sizing by a blood analyzer equipped with a DC impedance measurement device are known and are generally described in U.S. Pat. Nos. 2,656,508 and 3,810,011 which are incorporated herein by reference in their entireties.

In the analysis of DC impedance signals from the first suspension according to the method disclosed herein, a frequency histogram including platelets and red blood cells in the diluted blood sample can be generated. As illustrated in FIG. 1, the first platelet distribution D1 is a platelet DC impedance histogram $H_{Plt-D}$ from the first suspension, which represents size distribution of platelets 10a in the first suspension. In the histogram, the volume $Vol_p$ of platelets 10a is expressed in femtoliter (fL). As can be seen in FIG. 1, a portion of red blood cells 20 are immediate adjacent platelets 10a in the histogram.

The second suspension is a lysed blood sample. Red blood cells in a blood sample can be lysed by a lytic agent, such as cationic, nonionic, anionic, or amphiphilic surfactants and combinations thereof. Various known lysing reagents used for differential analysis of white blood cells on hematology analyzers may be used for lysing red blood cells in the second suspension in the present disclosure. The lysing reagents used for differential analysis of white blood cells on hematology analyzers are typically aqueous solutions containing one or more lytic agents, which may include cationic, nonionic, anionic or amphiphilic surfactants, or combinations thereof. In some embodiments, the lysing reagent may include one or more lytic agents for lysing red blood cells and a fluorescent dye which stains nucleated blood cells for differentiation of nucleated blood cells, such as white blood cells, from other cell types by light scatter and fluorescent measurements. One suitable example is the lysing reagent formulations described in U.S. Pat. No. 8,367,358, which is incorporated herein by reference in its entirety. As described in U.S. Pat. No. 8,367,358, the lysing reagents may comprise a cationic cyanine compound (a fluorescent dye), a cationic surfactant, a nonionic surfactant, and an anionic compound, and the lysing reagents may be used for lysing red blood cells and differentiating white blood cells into their subpopulations using fluorescent and light scatter measurements. Other known fluorescent dyes may also be used in the lysing reagents, such as the fluorescent dyes described in U.S. Pat. No. 8,273,329, which is incorporated herein by reference in its entirety. Moreover, in some embodiments, the fluorescent dye may be contained in a separate staining solution, which can be used together with a lysing reagent that does not contain a dye. Such a staining solution can be added to a blood sample before, after or simultaneously with the lytic agent to stain the nucleated blood cells.

The light scatter signals and fluorescent signals of the second suspension can be measured with one or more optical detectors equipped with an optical flow cell. Herein, optical flow cell refers to a focused-flow flow cell suitable for detection of light scatter signals and fluorescent signals, such as those used in existing flow cytometers and hematology analyzers. When a particle, such as a blood cell, passes through an orifice of the optical flow cell, an incident light beam from an illumination source directed at the aperture is scattered by the particle in all directions. The scattered light or light scatter signals can be detected by a photo-detector at various angles relative to the incident light beam. Different blood cell populations have different light scattering properties, which can be utilized for differentiation of different cell populations. The light scatter signals detected near the incident light are often referred to as forward angle light scatter or small angle light scatter signals. In some embodiments, the forward angle light scatter signals may be measured from about 1° to about 10° from the incident light. In other embodiments, the forward angle light scatter signals may be measured from about 2° to about 6° from the incident light. The light scatter signals detected at about 90° from the incident light are commonly referred to as side scatter signals, and fluorescent signals emitted from blood cells stained by a fluorescent dye are typically detected at about 90° from the incident light beam. In some embodiments, the side scatter signals are measured from about 65° to about 115° from the incident light.

One or more optical detectors may be used for measuring the forward angle light scatter and side scatter signals and fluorescent signals from the second suspension. Various known designs of optical detection hardware can be used for the purpose of the present disclosure.

Figure 2:
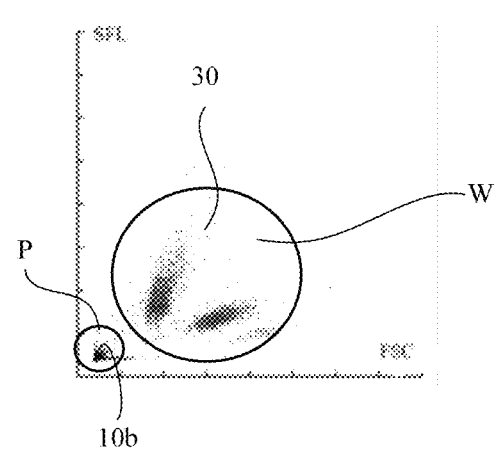
FIG. 2 shows a fluorescent (SFL) vs. forward angle light scatter (FSC) scattergram from a second suspension of the blood sample in FIG. 1.

In the analysis of the light scatter and fluorescent signals obtained from the second suspension according to the method disclosed herein, the platelets are differentiated from the white blood cells in the second suspension. As shown in FIG. 2, in a fluorescence (SFL) vs. forward angle light scatter (FSC) scattergram obtained from the second suspension of a blood sample, a platelet region P (platelet region herein refers to a region, in which platelets may exist, but not excluding that other particles and platelets overlap to some degree), in which platelets $10b$ in the second suspension locate, and a white blood cell region W, in which white blood cells $30$ locate, are clearly differentiated. Alternatively, a platelet region and a white blood cell region can also be separated in a fluorescence vs. side scatter (SSC) scattergram obtained from the second suspension of a blood sample.

Figures 3A, 3B, 3C:
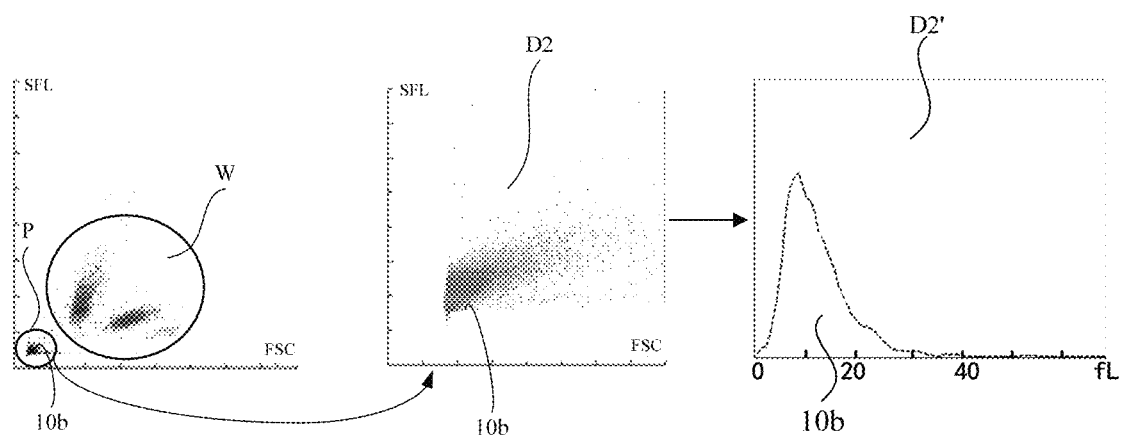

FIGS. 3A-5 further illustrate details of determining a platelet concentration in a blood sample in some embodiments of the present disclosure. The platelet region P is differentiated from the white blood cell region W as shown in FIG. 3A. A two-dimensional distribution of platelets $10b$ in the platelet region P is identified as shown in an enlarged view of the platelet region P in the SFL vs. FSC scattergram shown in FIG. 3B. The two-dimensional distribution of platelets $10b$ is one form of the second platelet distribution D2 obtained from the light scatter and fluorescent signals of the platelets in the second suspension.

In some embodiments as described hereinafter, the second platelet distribution D2 shown in FIG. 3B can be further converted to a derived platelet volume histogram $H_{Plt-L}$ using light scatter signals of platelets $10b$ in the platelet region P. The derived platelet volume histogram is another form of the second platelet distribution, as indicated by D2' in FIG. 3C, which is a one-dimensional distribution of the platelets in the second suspension.

Derived platelet volumes of the platelets in the second suspension can be calculated as a function of the light scatter signals of platelets $10b$ in the platelet region P. In one embodiment, a derived platelet volume Volpe of each platelet in the platelet region P may be calculated using equation (1):

$$\mathrm{Vol}_{p2} = \alpha * \mathrm{FSC} \qquad (1)$$

wherein FSC is the forward angle light scatter signal of an individual event in the platelet region, and α is a constant.

Alternatively, a derived platelet volume of each platelet in the platelet region P may also be calculated using equation (2):

$$\mathrm{Vol}_{p2a} = \beta * \exp(\gamma * \mathrm{FSC}) \qquad (2)$$

wherein FSC is the forward angle light scatter signal of an individual event in the platelet region, and β and γ are constants.

Moreover, the derived platelet volume of each platelet in the platelet region defined above may be calculated according to Mie scatter theory using forward angle light scatter and side scatter signals obtained from the second suspension. Furthermore, in the above calculation either using equation (1) or (2) or the Mie scatter theory, the derived platelet volume of the platelets in the second suspension is correlated with the platelet volume in the DC platelet histogram according to size correlation between the platelet volume in the DC platelet histogram and respective light scatter signals obtained from the second suspension. Therefore, in the derived platelet volume histogram $H_{Plt-L}$ shown in FIG. 3C, the size range of the platelets is the same as that in the platelet DC impedance histogram $H_{Plt-D}$ shown in FIG. 1. Herein, derived platelet volume histograms generated with derived platelet volumes obtained using equation (1) or (2), or Mie scatter theory are all referred to as the derived platelet volume histogram $H_{Plt-L}$.

Figure 4:
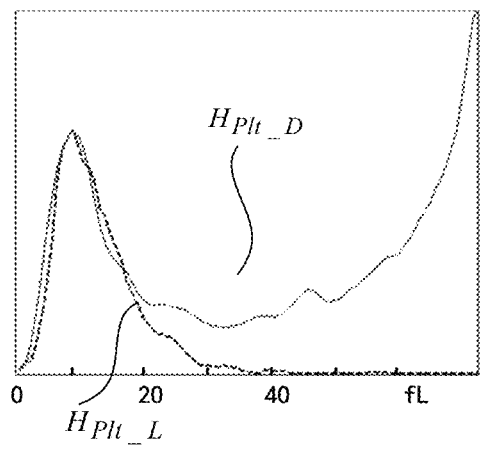
FIG. 4 is an overlay of a platelet DC impedance histogram $H_{Plt-D}$ from a first suspension and a derived platelet volume histogram $H_{Plt-L}$ from a second suspension of a blood sample which contains fragmented red blood cells.

FIG. 4 illustrates two overlaid histograms obtained using the method described above. As shown in FIG. 4, a platelet DC impedance histogram $H_{Plt-D}$ from the first suspension of a blood sample is overlaid with a derived platelet volume histogram $H_{Plt-L}$ from the second suspension of the blood sample, which is generated with derived platelet volumes ($Vol_{p2}$) obtained using equation (1). This blood sample used in the embodiment shown in FIG. 4 is an abnormal blood sample containing fragmented red blood cells as determined by the manual reference method. As shown in FIG. 4, the two histograms substantially overlap with each other, except that at the high end of platelet population, namely in a region from about 20 fL and above, the platelet DC impedance histogram ($H_{Plt-D}$) is elevated substantially due to interferences from the fragmented red blood cells. As can be appreciated, in the second suspension the red blood cells, including microcytes and fragmented red blood cells, are lysed. Therefore, in the derived platelet volume histogram $H_{Plt-L}$ obtained from the second suspension, the high end of the platelet population distribution reflects only in formation about platelets 10b, without an influence of interference materials from red blood cells such as microcytes and fragmented red blood cells. On the other hand, for blood samples containing large platelets, the derived platelet volume histogram $H_{Plt-L}$ obtained from the second suspension reflects the distribution of platelets 10b including the large platelets, without overlapping with the red blood cells as that would likely occur in the platelet DC impedance histogram obtained from the first suspension. The same also applies to blood samples containing giant platelets.

In some embodiments, after obtaining the derived platelet volume histogram $H_{Plt-L}$, the method generates a composite platelet histogram $H_{Plt-LD}$ as a function of the platelet DC impedance histogram $H_{Plt-D}$ of the first suspension and the derived platelet volume histogram $H_{Plt-L}$ of the second suspension: $H_{Plt-LD}=f(H_{Plt-L}, H_{Plt-D})$. The composite platelet histogram $H_{Plt-LD}$ incorporates information obtained from platelet measurements of both the first suspension and the second suspension.

In one exemplary embodiment, the composite platelet histogram is generated according to equation (3):

$$H_{Plt-LD}(i)=k_{i1}\times H_{Plt-L}(i)+k_{i2}\times H_{Plt-D}(i) \quad (i=1,2,\ldots,n) \quad (3)$$

wherein $H_{Plt-LD}$ (i) is event (i) in the composite platelet histogram; $H_{Plt-L}$ (i) is event (i) in the derived platelet volume histogram of the second suspension; $H_{Plt-D}$ (i) is event (i) in the platelet DC impedance histogram of the first suspension; and $k_{i1}$ and $k_{i2}$ are coefficients.

Figure 5:
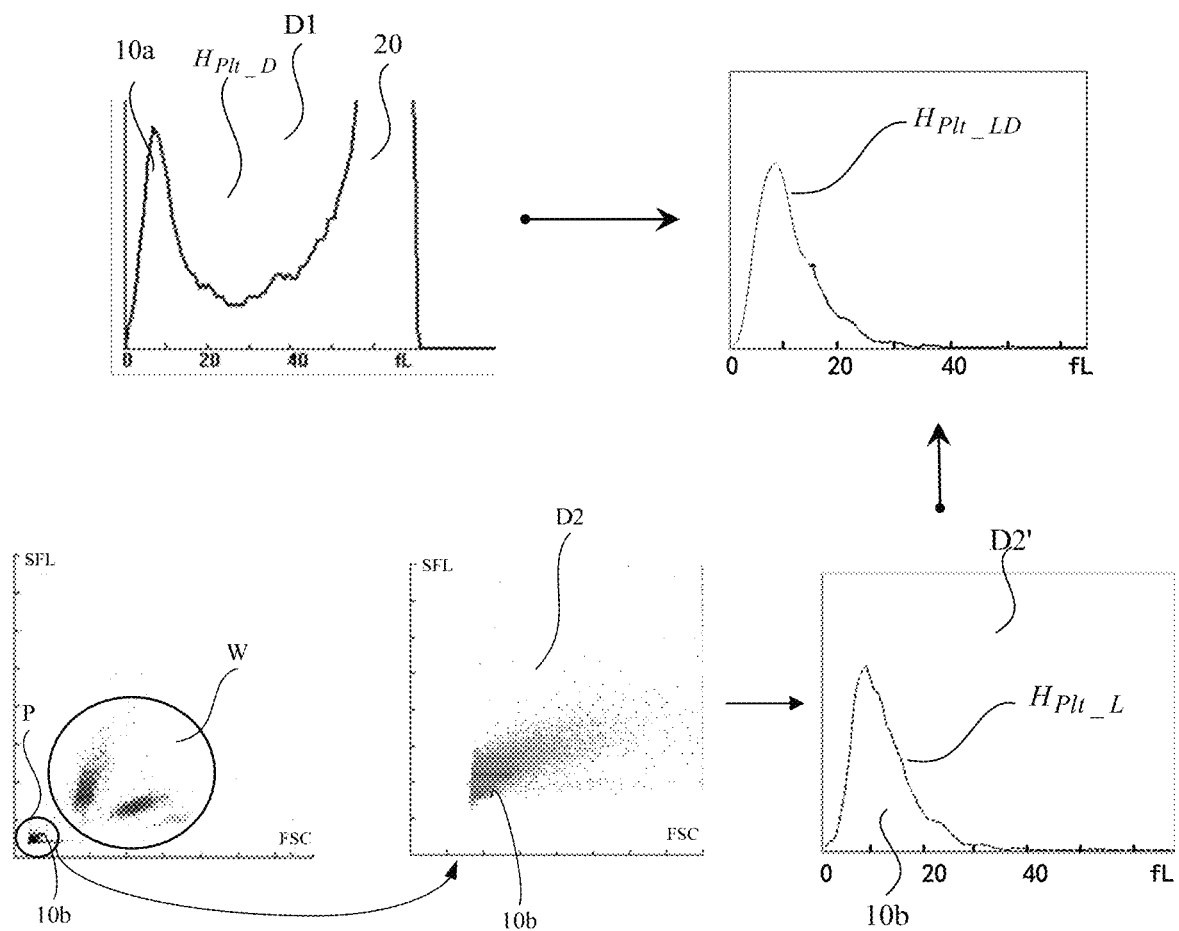
FIG. 5 illustrates a process of determining a platelet concentration using a composite platelet histogram $H_{Plt-LD}$ generated from a platelet DC impedance histogram $H_{Plt-D}$ and a derived platelet volume histogram $H_{Plt-L}$ in the embodiment of the present disclosure shown in FIG. 4.

In some embodiments, $k_{i1}$ and $k_{i2}$ in equation (3) may be constants. For example, in one exemplary embodiment, $k_{i1}$ and $k_{i2}$ are established according to the following criteria:

when $Vol_p(i)>20$ fL, $k_{i1}=1$, and $k_{i2}=0$; and when $Vol_p(i)\leq 20$ fL, $k_{i1}=0$, and $k_{i2}=1$ FIG. 5 further illustrates the process described above and a composite platelet histogram $H_{Plt-LD}$ generated with the above criteria using the abnormal blood sample shown in FIG. 4. In the composite platelet histogram $H_{Plt-LD}$ shown in FIG. 5, the size range of the platelets is the same as that in the platelet DC impedance histogram $H_{Plt-D}$ shown in FIG. 1 and that in the derived platelet volume histogram $H_{Plt-L}$ shown in FIG. 3C. As shown in FIG. 5, in the composite platelet histogram $H_{Plt-LD}$ the elevation of the curve at the high end of the platelet population occurred in the platelet DC impedance histogram $H_{Plt-D}$ in FIG. 4 due to interferences of fragmented red blood cells in the blood sample has been corrected. The platelet concentration of the blood sample is then determined according to the area under the curve in the composite platelet histogram $H_{Plt-LD}$.

Alternatively, $k_{i1}$ and $k_{i2}$ in equation (3) may also be variables determined according to a platelet valley/peak ratio ($R_{v/p}$) in the platelet DC impedance histogram $H_{Plt-D}$ of the first suspension which is defined hereinafter. In an alternative embodiment, $k_{i1}$ and $k_{i2}$ may be determined by equations (4) and (5):

$$k_{i1}=1-k_{i2} \quad (4)$$

$$k_{i2}=K_{\_Coef}*R_{v/p}+e \quad (5)$$

wherein $K_{\_Coef}$ is a constant less than zero; e is a constant greater than zero; and if $k_{i1}<0$ according to equation (4), $k_{i1}=0$, and if $k_{i2}<0$ according to equation (5), $k_{i2}=0$, and the coefficients are substituted into the equation (3) to obtain the composite platelet histogram $H_{Plt-LD}$.

As can be appreciated, the composite platelet histogram $H_{Plt-LD}$ can be used as a third platelet distribution obtained using the first platelet distribution from the first suspension and the second platelet distribution from the second suspension, namely the derived platelet volume histogram. The platelet concentration is obtained from this third platelet distribution.

In another exemplary embodiment, a composite platelet histogram $H_{Plt-LDa}$ may be generated using the platelet DC impedance histogram $H_{Plt-D}$ obtained from the first suspension and the derived platelet volume histogram $H_{Plt-L}$ obtained from the second suspension as described above according to a criterion defined by equations (6) and (7):

$$\text{when } Vol_p(i)>15 \text{ fL}, H_{Plt-LDa}(i)=\min(H_{Plt-L}(i), H_{Plt-D}(i)) \quad (i=1,2,\ldots,n) \quad (6)$$

$$\text{when } Vol_p(i)\leq 15 \text{ fL}, H_{Plt-LDa}(i)=H_{Plt-D}(i) \quad (i=1,2,\ldots,n) \quad (7)$$

wherein $H_{Plt-LDa}(i)$ is event (i) in the composite platelet histogram; $H_{Plt-L}(i)$ is event (i) in the derived platelet volume histogram of the second suspension; $H_{Plt-D}(i)$ is event (i) in the platelet DC impedance histogram of the first suspension; and min represents for event i using the minimum number between the two histograms.

In the criterion defined by equations (6) and (7), the cut-off point of 15 fL is an empirical value, which may vary with instruments and/or reagents used with the method. Same as described above, the platelet concentration of a blood sample is then determined according to the area under the curve in the composite platelet histogram ($H_{Plt-LDa}$).

In a further embodiment, instead of using equation (1) or (2), or Mie scatter theory, a derived platelet volume histogram $H_{Plt-Lb}$ may be generated by a curve fitting process using the light scatter signals of platelets 10b in the platelet region (P) in the SFL vs. FSC scattergram of the second suspension. In the derived platelet volume histogram $H_{Plt-Lb}$, derived platelet volumes $Vol_{p2b}$ for individual events are expressed by equation (8):

$$Vol_{p2b}=[1/(FSC*\sigma(2\pi)^{1/2})]\exp(-(\ln FSC-\mu)^2/2\sigma^2) \quad (8)$$

wherein FSC is the forward angle light scatter signal of an individual event in the platelet region in the SFL vs. FSC scattergram, $\mu$ and $\sigma$ are fitting parameters of the fitted curve.

In this embodiment, a composite platelet histogram $H_{Plt-LDb}$ may be generated using the derived platelet volume histogram $H_{Plt-Lb}$ obtained using equation (8) and the platelet DC impedance histogram $H_{Plt-D}$ obtained from the first suspension according to a criterion defined by equations (9) and (10):

$$\text{when Vol}_p(i) > 12 \text{ fL}, H_{Plt\text{-}LDb}(i) = H_{Plt\text{-}Lb}(i)$$
$$(1=1,2,\ldots,n) \quad (9)$$

$$\text{when Vol}_p(i) \leq 12 \text{ fL}, H_{Plt\text{-}LDb}(i) = H_{Plt\text{-}D}(i)$$
$$(1=1,2,\ldots,n) \quad (10)$$

wherein $H_{Plt\text{-}LDb}(i)$ is event (i) in the composite platelet histogram; $H_{Plt\text{-}Lb}(i)$ is event (i) in the derived platelet volume histogram obtained with equation (8) from the second suspension; and $H_{Plt\text{-}D}(i)$ is event (i) in the platelet DC impedance histogram of the first suspension.

In the criterion defined by equations (9) and (10), the cut-off point of 12 fL is an empirical value, which may vary with instruments and/or reagents used with the method. Same as described above, the platelet concentration of a blood sample is then determined according to the area under the curve in the composite platelet histogram $H_{Plt\text{-}LDb}$.

As can be appreciated, the composite platelet histogram $H_{Plt\text{-}LDb}$ can be generated using the derived platelet volume histogram $H_{Plt\text{-}Lb}$ obtained using equation (8) and the platelet DC impedance histogram $H_{Plt\text{-}D}$ obtained from the first suspension according to any method related to equation (3) as described above. Similarly, the composite platelet histogram $H_{Plt\text{-}LDa}$ can be generated using the platelet DC impedance histogram $H_{Plt\text{-}D}$ obtained from the first suspension and the derived platelet volume histogram $H_{Plt\text{-}L}$ obtained from the second suspension according to a criterion defined by equations (9) and (10).

In yet another embodiment, the platelet DC impedance histogram $H_{Plt\text{-}D}$ obtained from the first suspension and the derived platelet volume histogram $H_{Plt\text{-}L}$ obtained using equation (1) or (2), or Mie scatter theory, or the derived platelet volume histogram $H_{Plt\text{-}Lb}$ obtained using equation (8) from the second suspension as described above can be used to determine a platelet concentration of a blood sample according to the following process.

Figure 6A:
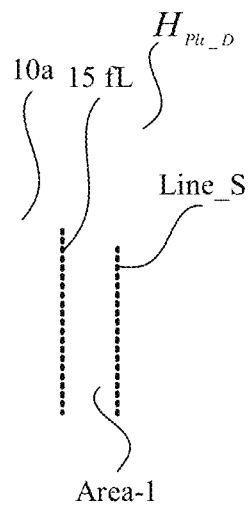
FIGS. 6A and 6B show a platelet DC impedance histogram $H_{Plt-D}$ and a derived platelet volume histogram $H_{Plt-L}$ of a blood sample for illustrating a process of determining a platelet concentration of the blood sample in a further embodiment.
Figure 6B:
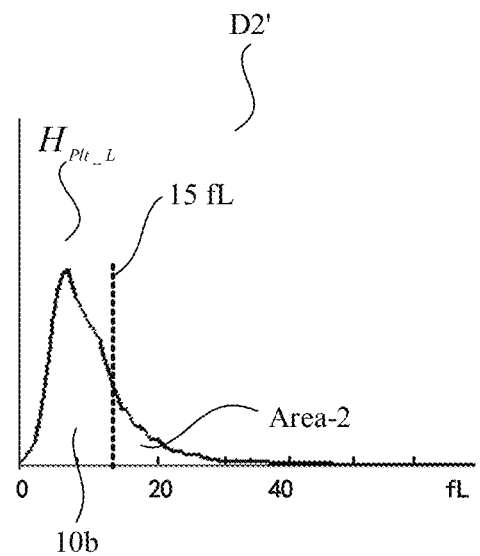

As shown in FIG. 6A, in this embodiment an area under the curve in the platelet DC impedance histogram $H_{Plt\text{-}D}$ obtained from the first suspension between a line representing the platelet volume (Vol$_p$) at 15 fL and Line-S which represents the bottom of a valley between the platelets and the red blood cells in the histogram is calculated and designated as Area-1. As further shown in FIG. 6B, an area under the curve in the derived platelet volume histogram $H_{Plt\text{-}L}$ obtained from the second suspension from a line representing the derived platelet volume Volpe at 15 fL to the right is calculated and designated as Area-2. Area-2 correlates with the platelets in the histogram having a volume greater than 15 fL. Then, an absolute difference δ between Area-1 and Area-2 is compared with a predetermined area threshold $A_T$. The predetermined area threshold $A_T$ is an empirical value. The platelet concentration of a blood sample is calculated using equations (11) and (12) according to a composing criterion which dictates that when δ>$A_T$, equation (11) is used, and when δ≤$A_T$, equation (12) is used:

$$C_{plt} = V_{HD}(1) + V_{HD}(2) + \ldots + V_{HD}(15) + V_{HL}(16) + V_{HL}(17) + \ldots + V_{HL}(n) \quad (11)$$

$$C_{plt} = V_{HD}(1) + V_{HD}(2) + \ldots + V_{HD}(15) + V_{HD}(16) + V_{HD}(17) + \ldots + V_{HD}(n) \quad (12)$$

wherein $V_{HD}$ (1, 2, n) is the value, or height, of the platelet DC impedance histogram $H_{Plt\text{-}D}$ at the position on the axis corresponding to the platelet volume of 1 fL, 2 fL, and n fL, respectively; $V_{HL}$ (1, 2, ... n) is the value, or height, of the derived platelet volume histogram $H_{Plt\text{-}L}$ at the position on the axis corresponding to the platelet volume of 1 fL, 2 fL, ... and n fL, respectively; and $C_{plt}$ is the platelet concentration.

In this embodiment, the cut-off point of 15 fL for calculation of Area-1 and Area-2 is determined empirically, which may vary with instruments and/or reagents used with the method. As can be appreciated, the platelet concentration $C_{plt}$ obtained using equations (11) and (12) is similar to that obtained by generating a composite platelet histogram $H_{Plt\text{-}LDc}$ by selecting respective parts of the platelet DC impedance histogram $H_{Plt\text{-}D}$ and the derived platelet volume histogram $H_{Plt\text{-}L}$ using the composing criterion described above. In other words, when δ≤$A_T$, the composite platelet histogram $H_{Plt\text{-}LDc}$ is generated using the platelet DC impedance histogram $H_{Plt\text{-}D}$, and when δ>$A_T$, the composite platelet histogram $H_{Plt\text{-}LDc}$ is generated using both $H_{Plt\text{-}D}$ and $H_{Plt\text{-}L}$, with the portion corresponding to platelet volume above 15 fL using the derived platelet volume histogram $H_{Plt\text{-}L}$. Then, the platelet concentration is calculated according to the area under the curve of the composite platelet histogram as described above.

The composite platelet histogram in various embodiments described above is a graphical representation of the distribution of platelet volume, which is a commonly used form of representing probability distribution of a continuous variable. Alternatively, the distribution of the platelet volume may also be expressed numerically in a form of table or list, with an equivalent or similar resolution of the histogram, or expressed by other suitable forms known in the art. Therefore, for the purpose of the present disclosure the composite platelet histogram described above can also be referred to as a composite platelet distribution which is not limited by its graphical representation. Similarly, the derived platelet volume histogram described above can also be referred to as a derived platelet volume distribution which is not limited by its graphical representation. Further, the platelet DC impedance histogram obtained from the first suspension described above can also be referred to as a DC platelet volume distribution which is not limited by its graphical representation.

Moreover, same as described above in reference to composite platelet histogram $H_{Plt\text{-}LD}$, the composite platelet distribution is a third platelet distribution obtained using the first platelet distribution from the first suspension and the second platelet distribution from the second suspension, and the platelet concentration is obtained from the third platelet distribution.

Furthermore, in the methods described herein the platelet region P in the SFL vs. FSC scattergram obtained from the second suspension can be differentiated from nucleated red blood cells in the case that abnormal blood samples contain nucleated red blood cells.

In further embodiments, the platelet concentration of a blood sample can be determined using the first platelet distribution from the first suspension and the second platelet distribution from the second suspension using a method described hereinafter in reference to FIGS. 7 through 10C.

Figure 7:
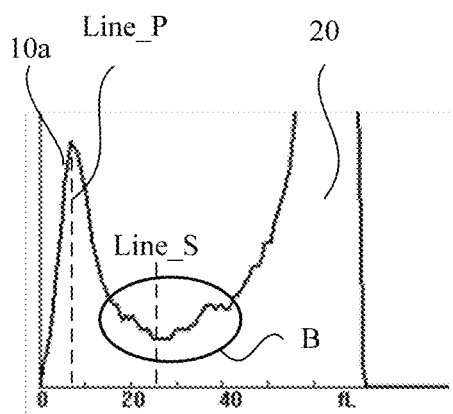
FIG. 7 is a platelet DC impedance histogram $H_{Plt-D}$ from a first suspension of a blood sample containing large platelets.

In one embodiment, the method includes determining a platelet valley/peak ratio $R_{v/p}$ in the platelet DC impedance histogram $H_{Plt\text{-}D}$ of the first suspension, and comparing the obtained platelet valley/peak ratio $R_{v/p}$ with a predetermined ratio threshold RT. As illustrated in FIG. 7, the platelet valley/peak ratio $R_{v/p}$ is determined by dividing the number of platelets at Line-S by the number of platelets at the peak of the platelets as indicated by Line-P, or in other words, by dividing the height of the curve at Line-S by the height of the peak at Line-P. As described above, Line-S represents the bottom of a valley between the platelets and the red blood cells in the histogram, and locates in a boundary area B between the two populations shown in FIG. 7. The predetermined ratio threshold $R_T$ may be determined using a large number of normal blood samples. For example, the predetermined ratio threshold $R_T$ may be a maximum platelet valley/peak ratio of normal blood samples.

Figure 8:
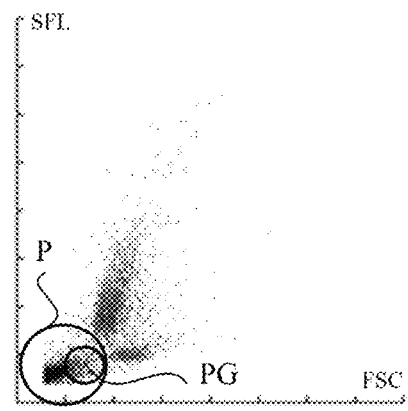
FIG. 8 illustrates a designated area within the platelet region in a SFL vs. FSC scattergram from a second suspension of the same blood sample in FIG. 7.

As further illustrated in FIG. 8, the method then determines the number of events N that are present in a designated area PG within the platelet region P in the SFL vs. FSC scattergram of the second suspension. The population in the platelet region P and the designated area PG shown in FIG. 8 can be more clearly seen in an enlarged view of FIG. 9A. It has been found that the events present in the designated area $P_G$ within the platelet region correlate with large platelets, and in normal blood samples only a limited number of events appear in this designated area. Therefore, an elevation of the number of events N in the designated area $P_G$ indicates a potential interference to DC impedance measurement of platelets in the first suspension due to overlap of the large platelets with red blood cells, and the extent of elevation further reflects the extent of the potential interference. The elevation of the number of events N in the designated area $P_G$ can be assessed according to a predetermined event threshold $G_T$. The predetermined event threshold $G_T$ may be determined with a large number of normal blood samples, which reflects a maximum number of events located in the designated area $P_G$ in normal blood samples. In analysis of a blood sample, if the measured N exceeds $G_T$, it indicates an abnormal elevation of events in the designated area $P_G$.

Once the platelet valley/peak ratio $R_{v/p}$ and the number of events N in the designated area $P_G$ are determined for a blood sample, the method determines a derived separation threshold Td in the valley between the platelets and the red blood cells in the platelet DC impedance histogram obtained from the first suspension for separating the platelets from the red blood cells using these parameters.

In one embodiment, the derived separation threshold $T_d$ can be determined according to equation (13):

$$T_d = T_{ap} + F_{of} \quad (13)$$

wherein $T_{ap}$ is an apparent separation threshold determined using the conventional method for separating the platelets from the red blood cells in the platelet DC impedance histogram $H_{Plt-D}$ of the first suspension, which is determined according to the bottom of the valley between the two populations and known size range of platelets; and $F_{of}$ is an offset that is a function of the platelet valley/peak ratio $R_{v/p}$ in the platelet DC impedance histogram ($H_{Plt-D}$) from the first suspension and the number of events N in the designated area $P_G$ within the platelet region P in the SFL vs. FSC scattergram from the second suspension described above.

In one exemplary embodiment, $F_{of}$ can be determined using equation (14) or (15) below according to an offset criterion:

$$F_{of} = b_1 * R_{v/p} - b_2 * N + c \quad (14)$$

wherein $R_{v/p}$ is the platelet valley/peak ratio in the platelet DC impedance histogram $H_{Plt-D}$ of the first suspension; N is the number of events present in the designated area $P_G$ within the platelet region P in the SFL vs FSC scattergram of the second suspension; $b_1$, $b_2$ are constants greater than 0; and c is a constant.

$$F_{of} = b_{11} * R_{v/p} + b_{21} * N + c_1 \quad (15)$$

wherein $R_{v/p}$ and N are the same as in equation (14); $b_{11}$, $b_{21}$ are constants greater than 0; and $c_1$ is a constant.

The offset criterion dictates that if $R_{v/p}$ exceeds $R_T$, and N is below $G_T$, equation (14) is applied for determining the derived separation threshold $T_d$ defined in equation (13); and if $R_{v/p}$ exceeds $R_T$, and N also exceeds $G_T$, equation (15) is applied for determining the derived separation threshold $T_d$ defined in equation (13). Moreover, according to the offset criterion, if $R_{v/p}$ does not exceed $R_T$, neither equation (14) nor (15) is applied, in other words, $F_{of}$ is zero in equation (13).

Once the derived separation threshold $T_d$ is obtained according to equations (13)-(15) and the offset criterion, the derived separation threshold $T_d$ is used to separate the two cell populations in the platelet DC impedance histogram $H_{Plt-D}$ of the first suspension, namely, to separate the platelets from the red blood cells. The platelet concentration of the blood sample is then determined according to the area under the curve for the platelet population as defined by the derived separation threshold $T_d$ in the histogram.

FIGS. 9A-9C and 10A-10C respectively illustrate the process for determining a platelet concentration of an abnormal blood sample using the methods described above. FIGS. 9A-9C illustrate the process for determining a platelet concentration in an abnormal blood sample containing large platelets. As shown in FIG. 9A, in the SFL vs. FSC scattergram from the second suspension of the blood sample, a large number of events N appeared in the designated area $P_G$, as such N exceeded the predetermined event threshold $G_T$. On the other hand, in the platelet DC impedance histogram $H_{Plt-D}$ of the first suspension shown in FIG. 9B, the platelet valley/peak ratio $R_{v/p}$ also exceeded the predetermined ratio threshold $R_T$. Therefore, according to the offset criterion described above, equation (15) was applied in determining the offset $F_{of}$. As shown in FIG. 9C, in the platelet DC impedance histogram $H_{Plt-D}$ from the first suspension of this blood sample, the derived separation threshold $T_d$ obtained from equation (13) was right shifted from the apparent separation threshold Tap, and the extent of the shift is dictated by $F_{of}$ obtained from equation (15).

In the example shown in FIGS. 9A-9C, the platelet concentration according to a flow cytometer reference method was $87 \times 10^9$/L, while the platelet concentration reported by a conventional impedance measurement method using the apparent separation threshold Tap shown in FIG. 9C was $63 \times 10^9$/L, which was substantially lower than the result of the flow cytometer reference method. However, using the derived separation threshold $T_d$ obtained using equation (13) and the offset criterion described above, the platelet concentration obtained was $84 \times 10^9$/L. Because of the ability to assess the presence of large platelets in the SFL vs. FSC scattergram of the second suspension and the ability of compensating for the effect of the large platelets to the platelet DC impedance histogram $H_{Plt-D}$, the present method enables correction of substantial errors that frequently occur with conventional impedance methods in measuring platelet concentrations of blood samples containing large platelets.

FIGS. 10A-10C further illustrate the process for determining a platelet concentration of an abnormal blood sample that contains fragmented red blood cells. As shown in FIG. 10B, in the measurement of this blood sample the platelet valley/peak ratio $R_{v/p}$ in the platelet DC impedance histogram $H_{Plt-D}$ from the first suspension exceeded the predetermined ratio threshold $R_T$; however, the number of events N in the designated area $P_G$ in the SFL vs. FSC scattergram from the second suspension was normal and did not exceed the predetermined event threshold $G_T$, see FIG. 10A.

According to the offset criterion described above, equation (14) was applied in determining the offset $F_{of}$. As shown in FIG. 10C, in the platelet DC impedance histogram $H_{Plt\text{-}D}$ from the first suspension of this blood sample, the derived separation threshold $T_d$ obtained from equation (13) was left shifted from the apparent separation threshold Tap and the extent of shift was dictated by $F_{of}$ obtained from equation (14). In this example, the platelet concentration according to the flow cytometer reference method was $46 \times 10^9$/L, while the platelet concentration reported by the conventional impedance measurement method using an apparent separation threshold Tap shown in FIG. 10C was $66 \times 10^9$/L, which was more than 40% higher than the result of the reference method. However, using equation (13) and the offset criterion described above, the platelet concentration obtained was $42 \times 10^9$/L. Therefore, the present method enables correction of substantial errors due to interferences of fragmented red blood cells in determining the platelet concentration using the conventional impedance measurement method.

Furthermore, in some embodiments the derived separation threshold can also be determined according to equation (16):

$$T_d' = T_{ap} + g^*(N - G_T) + h^*(R_{v/p} - R_T) + s \quad (16)$$

wherein N is the number of events present in the designated area $P_G$ within the platelet region P in the SFL vs FSC scattergram of the second suspension, $G_T$ is the predetermined event threshold, $R_{v/p}$ is the platelet valley/peak ratio in the platelet DC impedance histogram $H_{Plt\text{-}D}$ of the first suspension, and $R_T$ is the predetermined ratio threshold; g, h and s are constants, wherein g, h and s=0, when $R_{v/p} \leq R_T$.

In determining a platelet concentration of a blood sample using equation (16), the derived separation threshold $T_d'$ is calculated as a function of N and $R_{v/p}$ obtained from the analysis of light scatter and fluorescent signals of the second suspension and the analysis of DC impedance signals of the first suspension, respectively, as described above. The platelets are separated from the red blood cells in the platelet DC impedance histogram $H_{Plt\text{-}D}$ of the first suspension using the derived separation threshold $T_d'$ obtained from equation (16), in the same manner as illustrated in FIGS. 9C and 10C. The platelet concentration of the blood sample is then determined based on the area under the curve for the platelet population as defined by the derived separation threshold $T_d'$ in the histogram.

As can be appreciated, in the embodiments described in reference to equations (13)-(16), the platelet DC impedance histogram from the first suspension with the derived separation threshold separating the platelets and the red blood cells is another third platelet distribution obtained using the first platelet distribution from the first suspension and the second platelet distribution from the second suspension, namely a two dimensional distribution of platelets in the platelet region in the scattergram described above. The platelet concentration is obtained from this third platelet distribution.

As can be appreciated, in any embodiment described above, platelet data of various forms can be obtained using the third platelet distribution, for example, the composite platelet histograms $H_{Plt\text{-}LDa}$, $H_{Plt\text{-}LDb}$, $H_{Plt\text{-}LDc}$, or the curve for the platelet population as defined by the derived separation threshold $T_d'$ in the platelet DC impedance histogram. The obtained platelet data includes but is not limited to a platelet count (PLT), mean platelet volume (MPV), platelet distribution width (PDW), thrombocytocrit (PCT), etc.

Figure 12:
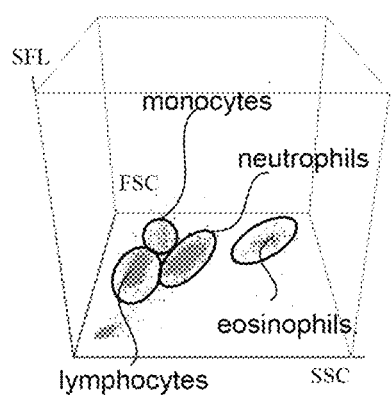
FIG. 12 shows a three-dimensional scattergram of SFL, SSC and FSC from a second suspension of a blood sample illustrating differentiation of white blood cell subpopulations in one embodiment of the present disclosure.
Figure 13:
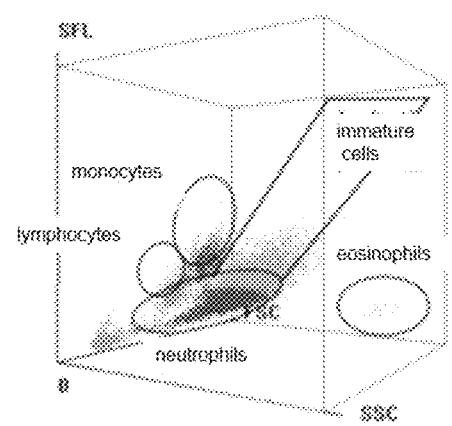
FIG. 13 shows a three-dimensional scattergram of FSC, SSC and SFL from a second suspension of a blood sample illustrating differentiation of immature cells in one embodiment of the present disclosure.

Moreover, in some embodiments the present method may further include differentiating white blood cells into subpopulations using the light scatter and fluorescent signals of the second suspension. Main white blood cell subpopulations include lymphocytes, monocytes, neutrophils, eosinophils and basophils. FIG. 12 shows a three-dimensional scattergram of SFL, SSC and FSC, illustrating differentiation of white blood cells into four subpopulations, namely, lymphocytes, monocytes, neutrophils, eosinophils using fluorescent signals, side scatter signals and forward angle light scatter signals obtained from the second suspension of a blood sample. Moreover, in further embodiments basophils may be differentiated from other white blood cell subpopulations using the light scatter and fluorescent signals of the second suspension. In addition, the present method may further include enumerating the number of the white blood cells in the second suspension to report a white blood cell count of a blood sample. One skilled in the art should understand that, the present method may further include identifying nucleated red blood cells, immature cells or blast cells using the light scatter and fluorescent signals of the second suspension. For example, as shown in FIG. 13, if immature cells are present in a blood sample, the present method can use the light scatter and fluorescent signals of the second suspension to identify the immature cells and differentiating the white blood cells into four subpopulations, namely, lymphocytes, monocytes, neutrophils, eosinophils.

Figure 15:
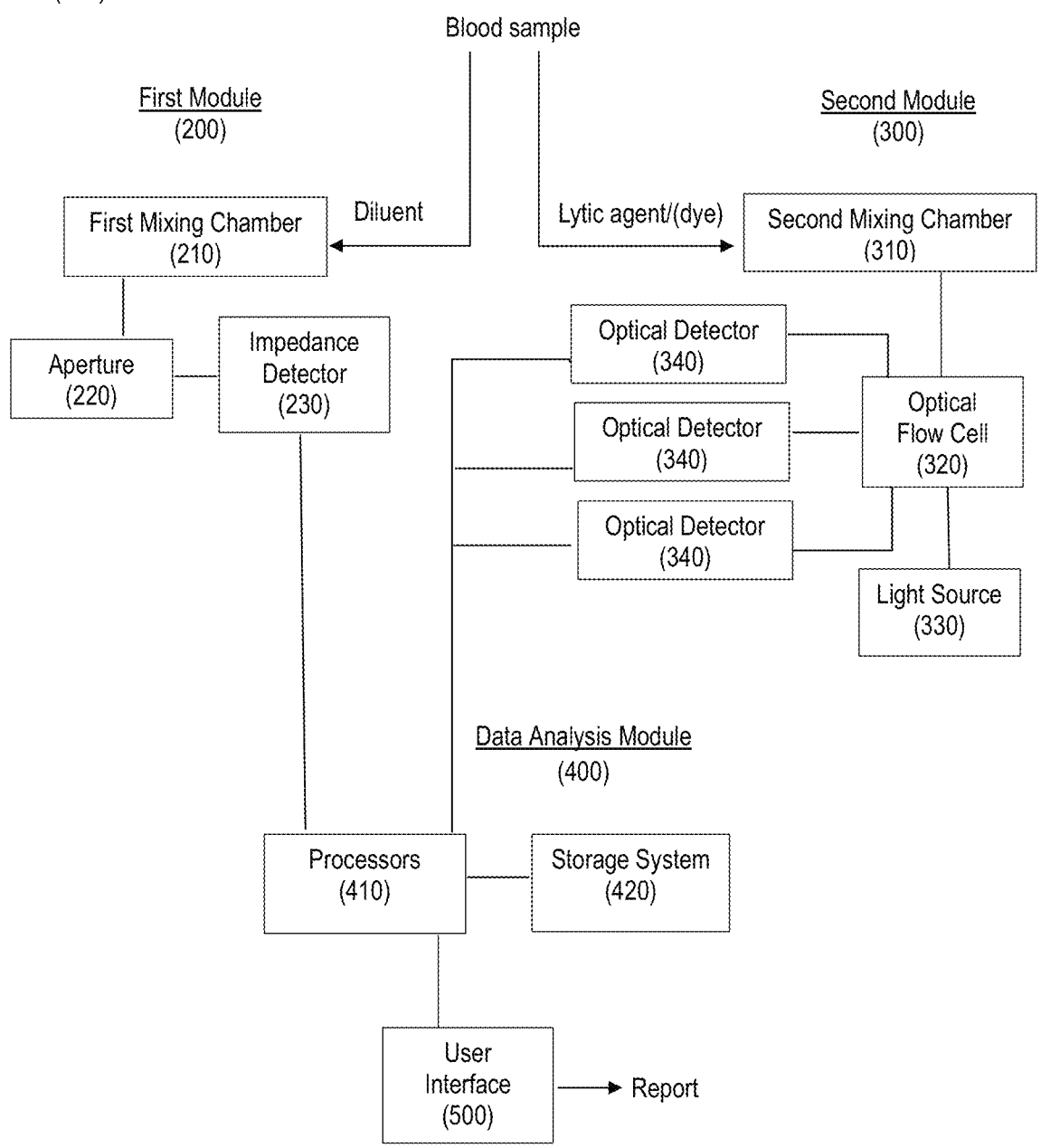
FIG. 15 is a simplified block diagram of a hematology system according to the present disclosure.

FIG. 15 shows a simplified block diagram of a hematology system 100 that carries out the methods described herein. The hematology system 100 may include a first module 200, a second module 300, and a data processing module 400. The first module 200 includes a first mixing chamber 210 configured to mix an aliquot of a blood sample with a diluent to form the first suspension, and a DC impedance detector 230 with electrodes arranged with an aperture 220 in a flow path connected with the first mixing chamber 210. The DC impedance detector 230 is configured to measure DC impedance signals of the first suspension passing through the aperture 220.

The second module 300 includes a second mixing chamber 310 configured to mix an aliquot of a blood sample with a lytic agent and a fluorescent dye to form the second suspension, a light source 330 configured with its light beam aimed at an orifice of an optical flow cell 320 in a flow path connected with the second mixing chamber 310, and one or more optical detectors 340 equipped with the optical flow cell 320 and configured to measure light scatter signals and fluorescent signals of the second suspension passing through the orifice of the optical flow cell 320. In one exemplary embodiment, the hematology system 100 may include a red semiconductor laser with an emission wavelength of 640 nm as the light source, and three optical detectors enabling detections of forward angle light scatter, side scatter and fluorescent signals, respectively. As described above, the forward angle light scatter signals may be measured from about 1° to about 10° or from about 2° to about 6° from the incident light beam, and the side scatter signals and fluorescent signals may be measured at about 90° from the incident light beam. In one exemplary embodiment, the forward angle light scatter signals may be measured from about 1° to about 10° and the side scatter signals may be measured from about 65° to about 115° from the incident light beam. Moreover, the system 100 may include one or more optical detectors configured to detect light scatter signals at other angles.

In the embodiment shown in FIG. 15, each of the first mixing chamber 210 and the second mixing chamber 310 is configured to prepare the respective hematology suspension. In an alternative embodiment, the hematology analyzer may have one shared mixing chamber used for preparing the first suspension and second suspension, respectively, for example, in a sequential manner. The shared mixing chamber may be cleaned with a diluent between preparations of the two different suspensions.

The data processing module 400 is operably connecting with the DC impedance detector 230 in the first module 200 and optical detectors 340 in the second module 300, respectively. As shown in FIG. 15, the data processing module 400 includes one or more processors 410 and a storage system 420 that can store basic programs and data constructs which provide the functionality of implementing the various aspects of the methods disclosed herein. Storage system 420 may include one or more memories and one or more non-transitory computer readable media. The non-transitory computer readable media may include hard disk drives, floppy disks, optical discs, secure digital memory card (SD), compact flash card, and the like. The memory may include a main random access memory (RAM) or dynamic RAM (DRAM) for storage of instructions and data during execution of the computer programs and a read only memory (ROM) in which fixed instructions may be stored. The non-transitory computer readable medium is programmed with a computer application program that implements the functionality of the methods described herein and can be executed by one or more processors 410. When executed by the processor, the computer application program stored in the non-transitory computer readable medium causes the processor to determine the platelet concentration of a blood sample according to the methods described herein and to perform differentiation and enumeration of the white blood cells, or identification of the nucleated red blood cells, the immature cells or the blast cells according to the methods described herein.

The data processing module 400 is configured to carry out various aspects of the methods described herein. The DC impedance signals detected in the first module and the light scatter and fluorescent signals detected in the second module may be processed, respectively, in real time. In exemplary embodiments, these signals may be processed using Field-Programmable Gate Array (FPGA), Digital Signal Processing (DSP), or CPU. Then, the processed DC impedance signals, light scatter signals and fluorescent signals are analyzed automatically with the programed computer applications to obtain the first and second platelet distributions and determine the platelet concentration of a blood sample according to the methods described herein. Moreover, the signals from the second module are also used for differentiation and enumeration of the white blood cells, or for identification of the nucleated red blood cells, the immature cells or the blast cells, according to the methods described herein.

The hematology system 100 further includes a user interface 500 which includes user interface input and output devices. The results obtained by the methods described herein may be displayed on a user interface output device, such as a computer screen. In addition to the platelet concentration and white blood cell differential results obtained using the methods described herein, graphic results may be generated on the screen display, such as a composite platelet histogram $H_{Plt-LD}$ shown in FIG. 5 or a composite platelet histogram $H_{Plt-LDa}$, or $H_{Plt-LDb}$, a DC platelet histogram $H_{Plt-D}$ with a derived separation threshold $T_d$ shown in FIG. 9C or 10C, and 2-D or 3-D scattergram showing differentiation of white blood cell subpopulations. The display may further include information obtained in intermediate steps of the methods described herein, for example, the platelet DC impedance histogram $H_{Plt-D}$ of the first suspension, the derived platelet volume histogram $H_{Plt-L}$ or $H_{Plt-Lb}$, the overlay of $H_{Plt-D}$ and $H_{Plt-L}$ as shown in FIG. 4 or an overlay of $H_{Plt-D}$ and $H_{Plt-LD}$, the SFL vs. FSC scattergram and/or an enlarged view of the platelet region P shown in FIGS. 3A and 3B, and the designated area $P_G$ in the SFL vs. FSC scattergram as shown in FIGS. 9A and 10A. The display of platelet information may be presented in various forms, such as displayed together with analysis results of other cell types in a blood sample, displayed in a designated platelet screen, displayed in layered manner which allows the user to select a specific display of their interest, and other alternatives.

In a further embodiment, the method of determining a platelet concentration of a blood sample described above can also be accomplished with multi-angle light scatter measurements of the second suspension of the blood sample without the fluorescence measurement. More specifically, the present inventors discovered that side scatter signals or medium angle light scatter signals from the second suspension could be used for obtaining the second platelet distribution in replacement of the fluorescent signals in determining the platelet concentration of a blood sample with the methods described above. Herein, the medium angle light scatter signals are detected at an angle between the forward angle light scatter and the side scatter. In one exemplary embodiment, the forward angle light scatter signals may be detected from about 1° to about 10° and the side scatter signals may be detected from about 65° to about 115° from the incident light beam. In another exemplary embodiment, the forward angle light scatter signals may be detected from about 2° to about 6° from the incident light beam, and light scatter signals at a low medium angle from about 8° to about 24° may be detected. Herein, the latter is referred to as a low medium angle light scatter. Moreover, light scatter signals at a high medium angle from about 25° to about 65° from the incident light beam may be detected, which is referred as a high medium angle light scatter.

Figure 11A:
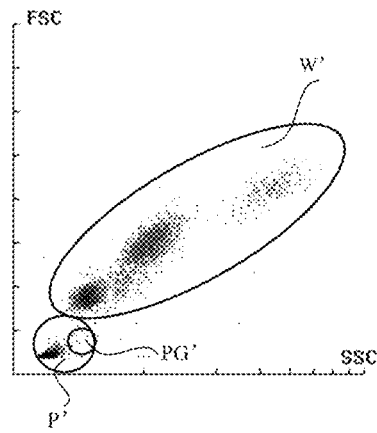
FIGS. 11A and 11B are forward angle light scatter (FSC) vs. side scatter (SSC) scattergrams from a second suspension from a normal blood sample and an abnormal blood sample containing large platelets, respectively, according to a further embodiment of the present disclosure.
Figure 11B:
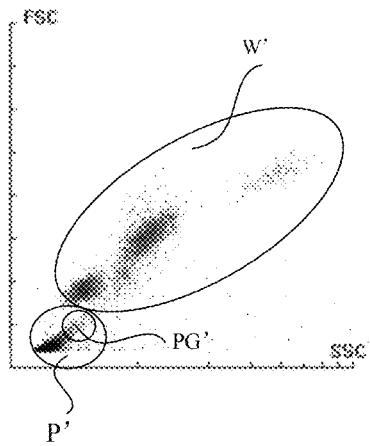

The method in this embodiment is further described in reference to FIGS. 11A and 11B. FIGS. 11A and 11B illustrate a forward angle light scatter (FSC) vs. side scatter (SSC) scattergram obtained from the second suspension of a normal blood sample and an abnormal blood sample containing large platelets, respectively. As shown, a platelet region P' is differentiated from a white blood cell region Win the FSC vs. SSC scattergram. Same as in the methods using fluorescent and light scatter measurements described above, in this embodiment the second platelet distribution may be in the form of a two-dimensional distribution of the platelets in the platelet region P' shown in FIGS. 11A and 11B, or in the form of a derived platelet volume histogram as described above in reference to FIG. 3C as a one-dimensional distribution. The second platelet distribution obtained from the light scatter signals of the second suspension can be used together with the first platelet distribution obtained from the first suspension for determining the platelet concentration of a blood sample in the same manner as described above.

More specifically, a platelet concentration of a blood sample may be determined using the process described above in reference to equations (1)-(3). In this embodiment, a derived platelet volume histogram $H_{Plt-L'}$ can be obtained from the second suspension using forward angle scatter signals of the platelets in the platelet region P' in the FSC vs.

SSC scattergram according to equation (1) or (2) in the same manner as described above, or using the forward angle light scatter and side scatter signals of the platelets in the platelet region P' according to the Mie scatter theory as described above. Then, a composite platelet histogram $H_{Plt-LD'}$ is generated according to equation (3) using the platelet DC impedance histogram H plt-D from the first suspension and the derived platelet volume histogram $H_{Plt-L}'$ from the second suspension. In this embodiment, event (i) in the derived platelet volume histogram $H_{Plt-L}$ substituted into equation (3) is event (i) in the derived platelet volume histogram $H_{Plt-L'}$. The platelet concentration is then determined according to the area under the curve in the composite platelet histogram $H_{Plt-LD'}$.

Similarly, a platelet concentration of a blood sample may also be determined using the process described above in reference to composite platelet histogram $H_{Plt-LDa}$. In this embodiment, a composite platelet histogram $H_{Plt-LDa'}$ may be generated using the platelet DC impedance histogram $H_{Plt-D}$ obtained from the first suspension and the derived platelet volume histogram $H_{Plt-L'}$ obtained from light scatter signals of the platelets in the platelet region P' in the FSC vs. SSC scattergram described above according to equations (6) and (7). In this embodiment, event (i) in the derived platelet volume histogram $H_{Plt-L}$ substituted into equation (6) is event (i) in the derived platelet volume histogram $H_{Plt-L'}$. The platelet concentration is then determined according to the area under the curve in the composite platelet histogram $H_{Plt-LDa'}$.

Moreover, a platelet concentration of a blood sample may also be determined using the process described above in reference to composite platelet histogram $H_{Plt-LDb}$. In this embodiment, a composite platelet histogram $H_{Plt-LDb}$ may be generated according to the criterion defined by equations (9) and (10), using the platelet DC impedance histogram $H_{Plt-D}$ obtained from the first suspension and the derived platelet volume histogram $H_{Plt-Lb'}$ obtained from forward angle light scatter signals of the platelets in the platelet region P' in the FSC vs. SSC scattergram using equation (8). In this embodiment, event (i) in the derived platelet volume histogram $H_{Plt-L}$ substituted into equation (9) is event (i) in the derived platelet volume histogram $H_{Plt-L'}$. The platelet concentration is then determined according to the area under the curve in the composite platelet histogram $H_{Plt-LDb'}$.

In addition, a platelet concentration of a blood sample may also be determined using the process described above in reference to equations (11) and (12). In this embodiment, the platelet concentration can be calculated using equations (11) and (12) according to the composing criterion described above. In this embodiment, the elements in the derived platelet volume histogram $H_{Plt-L}$ defined in equation (11) are corresponding elements in the derived platelet volume histogram $H_{Plt-L'}$ obtained from light signals of the platelets in the platelet region P' in the FSC vs. SSC scattergram as described above; and in the composing criterion an absolute difference δ' is the absolute difference between the Area-1 in the platelet DC impedance histogram $H_{Plt-D}$ and Area-2' in the derived platelet volume histogram $H_{Plt-L'}$, which is further compared to a predetermined area threshold $A_T'$.

As described above, in the embodiments of using multi-angle light scatter measurements of the second suspension, the composite platelet histogram such as $H_{Plt-LDa'}$ or $H_{Plt-LDb'}$ is a third platelet distribution obtained using the first platelet distribution from the first suspension and the second platelet distribution from the second suspension, namely, respective derived platelet volume histogram described herein. The platelet concentration is obtained from the third platelet distribution.

Furthermore, the platelet concentration may be determined using the process described above in reference to equations (13)-(15). As shown in FIG. 10B for illustrating the method of determining the platelet concentration without fluorescent signals, in this blood sample a large number of events appeared in the designated area $P_G'$ within the platelet region P' in the FSC vs. SSC scattergram from the second suspension. In this embodiment, such information from the second platelet distribution may be used together with the platelet valley/peak ratio $R_{v/p}$ in the platelet DC impedance histogram $H_{Plt-D}$ from the first suspension to determine the offset $F_{of}$ and the derived separation threshold $T_d$ using equations (13)-(15) and the offset criterion in the same manner as described above. In this case, in equations (14) and (15), N is the number of events in the designated area $P_G'$ within the platelet region P' in the FSC vs. SSC scattergram from the second suspension. The derived separation threshold $T_d$ obtained is used to separate the platelets from the red blood cells in the platelet DC impedance histogram $H_{Plt-D}$ from the first suspension to obtain the platelet concentration as described above in reference to FIGS. 9C and 10C. In this embodiment, the predetermined event threshold $G_T$ may be determined using a large number of normal blood samples, which reflects a maximum number of events located in the designated area $P_G'$ within the platelet region P' in the FSC vs. SSC scattergram in normal blood samples.

Furthermore, in this embodiment the derived separation threshold $T_d$ may also be determined using equation (16), in which N is the number of events in the designated area $P_G'$ within the platelet region P' in the FSC vs. SSC scattergram from the second suspension, and $G_T$ is the predetermined event threshold in the designated area $P_G'$.

Corresponding to this embodiment, the hematology system carrying out the methods described above includes a second module that includes one or more optical detectors configured to detect forward angle light scatter signals and side scatter signals of the second suspension passing through the orifice of the optical flow cell, or configured to detect forward angle light scatter signals and medium angle light scatter signals of the second suspension passing through the orifice of the optical flow cell. In this case, the hematology system shown in FIG. 15 may include two optical detectors, one for detection of forward angle light scatter signals, and the other for detection of side scatter signals or medium angle light scatter signals of the second suspension.

Moreover, in this embodiment the data processing module is configured to analyze the DC impedance signals of the first suspension from the first module and the light scatter signals of the second suspension from the second module, respectively, and to implement various aspects of the method. In the same manner as described above in reference to FIG. 15, when executed by the processor, the computer applications stored in the non-transitory computer readable medium causes the processor to determine the platelet concentration according to the methods described herein, and to perform differentiation and enumeration of the white blood cells according to the methods described below.

As can be appreciated, in this embodiment the preparation of the second suspension does not require a fluorescent dye. The lysing reagents described above containing one or more lytic agents for lysing red blood cells in the second suspension, but without the fluorescent dye. Furthermore, various existing lysing reagents used for differential analysis of white blood cells on hematology analyzers may be used for preparing the second suspension, for example various lysing reagent formulations described in U.S. Pat. No. 7,413,905, which is incorporated herein by reference in its entirety. More specifically, as described U.S. Pat. No. 7,413,905, the lysing reagents may include one or more surfactants, as the lytic agent, for lysing red blood cells and partly damaging the cell membrane of white blood cells, an organic compound bearing an anionic group capable of binding to the cationic component present in the white blood cells to provide morphological differences among white blood cell subpopulations, and a buffer to adjust the reagent pH to 2-8. The lytic agents may include one or more cationic surfactants, one or more anionic surfactants, one or more ampholytic surfactants, a combination of one or more cationic surfactants and one or more ampholytic surfactants, or a combination of one or more anionic surfactants and one or more ampholytic surfactants.

This embodiment is advantageous in terms of instrument simplicity and low cost because no fluorescent measurement is required. This embodiment may be implemented on existing hematology analyzers that are equipped with forward angle light scatter and side scatter measurements, or forward angle light scatter and medium angle light scatter measurements. Moreover, since no fluorescent dye is needed, it substantially reduces the cost of the reagent. One skilled in the art can understand that, this embodiment is applicable for hematology analyzers with fluorescent measurement, which can simultaneously measure forward angle light scatter signals, side scatter signals and fluorescent signals.

Figure 14:
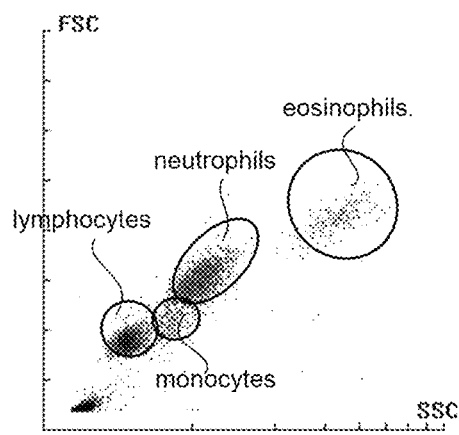
FIG. 14 shows a FSC vs. SSC scattergram from a second suspension of a blood sample illustrating differentiation of white blood cell subpopulations in a further embodiment of the present disclosure.

Moreover, the methods in this embodiment may further include differentiating white blood cells into subpopulations using the light scatter signals from the second suspension. FIG. 14 shows a FSC vs SSC scattergram illustrating differentiation of white blood cells into lymphocytes, monocytes, neutrophils, eosinophils using the light scatter signals obtained from the second suspension. Moreover, in further embodiments basophils may be differentiated from other white blood cell subpopulations using the light scatter signals of the second suspension. In addition, the method in this embodiment may further include enumerating the number of the white blood cells in the second suspension to report a white blood cell count of a blood sample.

Examples 1 to 7 further illustrate the methods of determining a platelet concentration of a blood sample described above. As shown in Example 1, a hematology analyzer enabling detections of forward angle light scatter, side scatter and fluorescent signals was used to determine platelet concentrations of 25 blood samples including 5 normal and 20 abnormal blood samples which contained fragment red blood cells, microcytes, or large platelets. The platelet concentrations of the same blood samples were also measured by a flow cytometer as a reference method, as well as by a conventional DC impedance measurement method for comparison.

Figure 16:
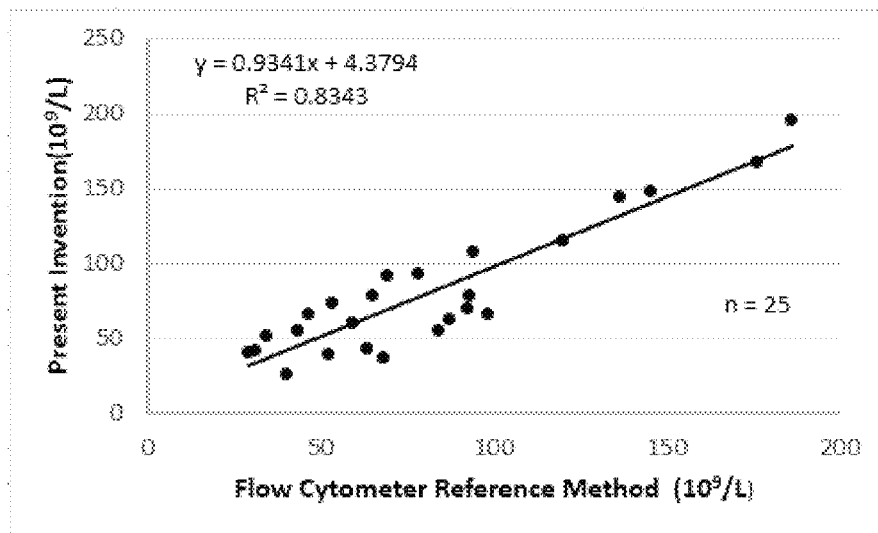
FIG. 16 shows a correlation of platelet concentrations of blood samples obtained using a conventional DC impedance method to platelet concentrations of these blood samples obtained using a flow cytometry reference method as described in Example 1.

FIG. 16 shows a correlation of the platelet concentrations of these blood samples obtained using the conventional DC impedance measurement method to the platelet concentrations of these blood samples obtained using the flow cytometry reference method. As shown, the platelet concentrations of these blood samples obtained using the conventional DC impedance measurement method correlated poorly with the results obtained using the reference method since a major portion of the blood samples were abnormal blood samples containing fragment red blood cells microcytes, or large platelets which were known to interfere with conventional impedance measurement of platelets. The correlation coefficient ($R^2$) in the linear regression analysis of the results of these 25 blood samples was 0.8343. It was found that the platelet concentrations of the blood samples containing fragmented red blood cells or microcytes obtained using the conventional DC impedance measurement method were substantially higher than the results obtained by the reference method. On the other hand, the platelet concentrations of the blood samples containing large platelets obtained using the conventional DC impedance measurement method were substantially lower than the results obtained by the reference method.

Figure 17:
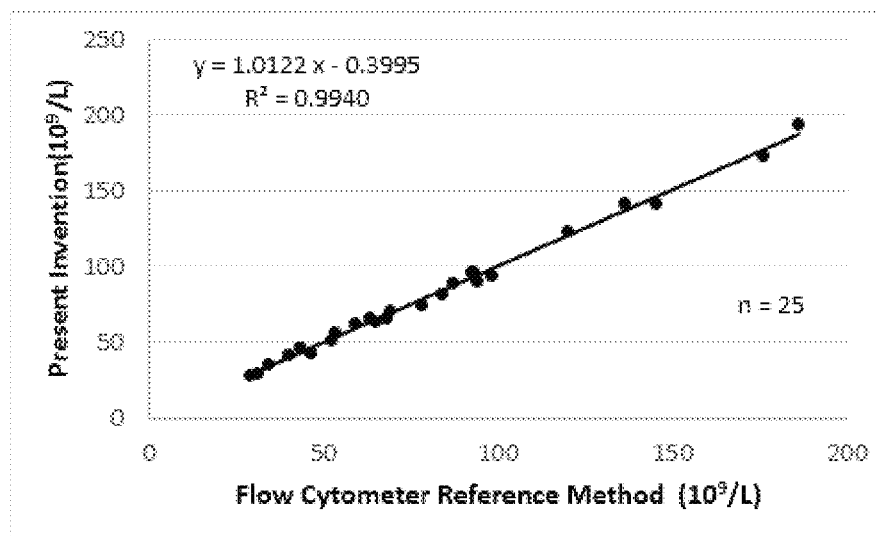
FIG. 17 shows a correlation of platelet concentrations of blood samples obtained using the method according to one embodiment of the present disclosure as described in Example 1 to platelet concentrations of these blood samples obtained using the flow cytometry reference method.

However, as shown in FIG. 17 the platelet concentrations of these 25 blood samples obtained using the composite platelet histogram $H_{Plt-LD}$ generated from equation (3) correlated closely with the results obtained by the flow cytometer reference method with a correlation coefficient ($R^2$) of 0.9940. As shown, substantial errors occurred in the conventional impedance method due to the presence of fragment red blood cells, microcytes, or large platelets in the abnormal blood samples were effectively corrected using the composite platelet histogram $H_{Plt-LD}$ described above.

Figure 18:
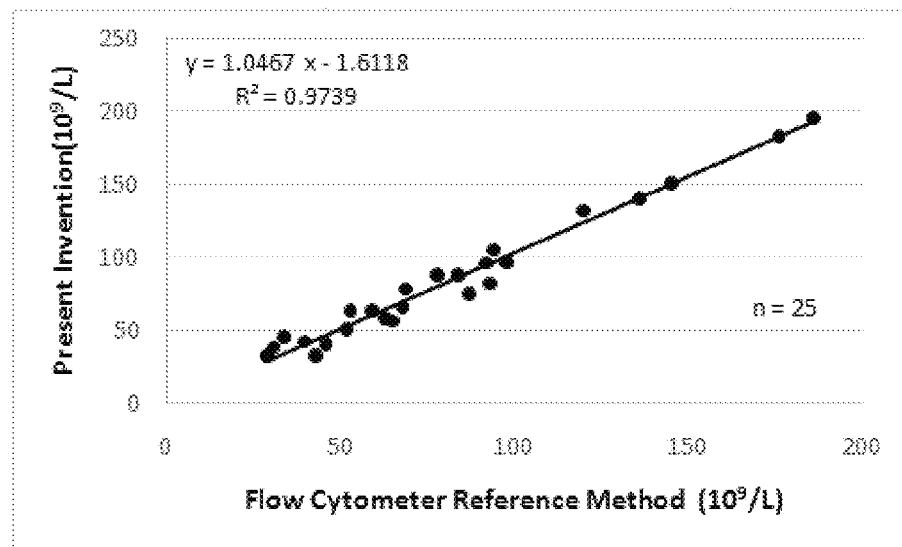
FIG. 18 shows a correlation of platelet concentrations of blood samples obtained using the method according to a further embodiment of the present disclosure as described in Example 2 to platelet concentrations of these blood samples obtained using the flow cytometry reference method.

Similarly, as shown in Example 2, the platelet concentrations of these 25 blood samples obtained using a composite platelet histogram $H_{Plt-LDa}$ generated according to the criterion defined in equations (6) and (7) correlated closely with the results obtained by the flow cytometer reference method with a correlation coefficient ($R^2$) of 0.9739, see FIG. 18. As further shown in Example 3, a composite platelet histogram $H_{Plt-LDb}$ was generated using a derived platelet volume histogram $H_{Plt-Lb}$ obtained from light scatter signals of platelets in the platelet region P using the curve fitting process defined by equation 8 described above. The platelet concentrations of these 25 blood samples obtained using the composite platelet histogram $H_{Plt-LDb}$ correlated closely with the results obtained by the flow cytometer reference method with a correlation coefficient ($R^2$) of 0.9681, see FIG. 19. Moreover, as shown in Example 4, the platelet concentrations of these 25 blood samples determined using equations (11) and (12) according to the composing criterion described above correlated closely with the results obtained by the flow cytometer reference method with a correlation coefficient ($R^2$) of 0.9797, see FIG. 20. In each of these three examples, the present methods enabled accurate measurements of platelet concentrations in the blood samples, and substantial errors occurred in the conventional impedance method due to the presence of fragment red blood cells, microcytes, or large platelets in the abnormal blood samples were effectively corrected.

Figure 21:
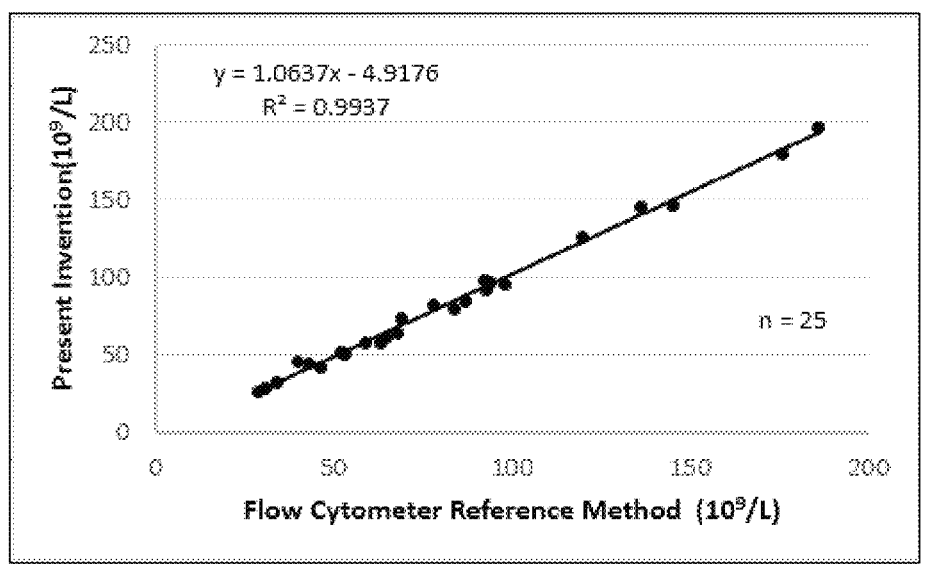
FIG. 21 shows a correlation of platelet concentration of blood samples obtained using the method according to another embodiment of the present disclosure as described in Example 5 to platelet concentration of these blood samples obtained using the flow cytometry reference method.

Example 5 further illustrates measurements of platelet concentrations of the blood samples using equations (13)-(15) and the offset criterion described above. The same 25 blood samples in Example 1 were used for the measurements. As shown in FIG. 21, the platelet concentrations of these blood samples obtained by the method using equations (13)-(15) correlated closely with the results obtained by the flow cytometer reference method with a correlation coefficient ($R^2$) of 0.9937. Same as in other examples, the method provided accurate measurements of platelet concentrations in the blood samples. The substantial errors occurred in the conventional impedance method due to the presence of fragment red blood cells, microcytes, or large platelets in the abnormal blood samples were effectively corrected using this method.

Figure 22:
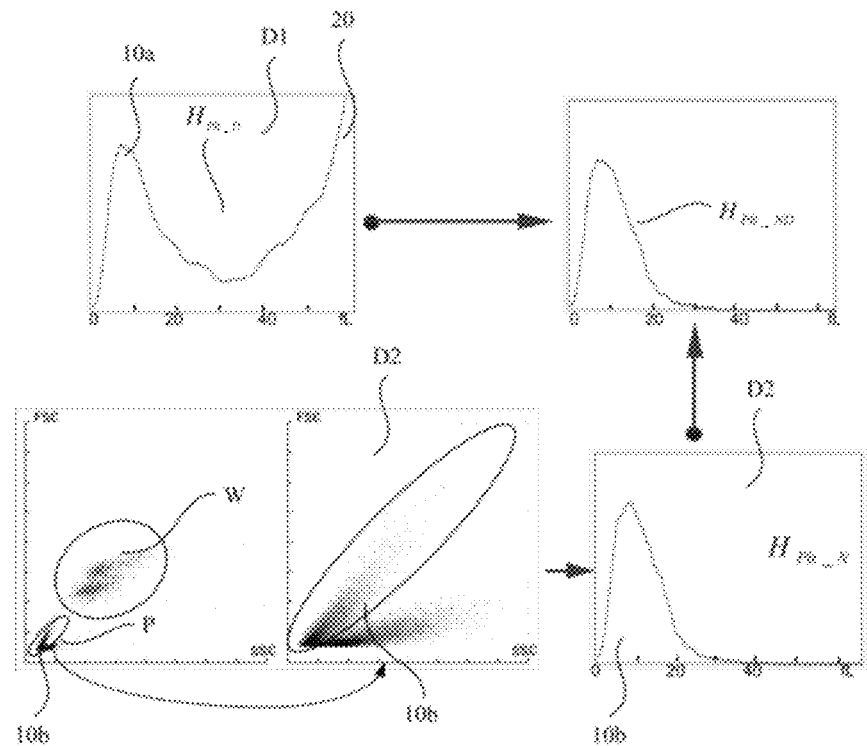
FIG. 22 illustrates a process of determining a platelet concentration using a composite platelet histogram $H_{Plt-LD}$ generated from a platelet DC impedance histogram $H_{Plt-D}$ and a derived platelet volume histogram $H_{Plt-L}$ in one embodiment of the present disclosure.

The methods for measuring platelets in Examples 1-5 were applied in the steps for differentiating white blood cells after lysing red blood cells. The method for measuring platelets as described in Example 6 was applied in the steps for differentiating nucleated red blood cell after lysing red blood cells. Examples 6 and 7 shows the composite platelet histogram $H_{Plt-LD}$ generated using equation (3) by the methods described above. FIG. 22 further shows the process for generating the composite platelet histogram $H_{Plt-LD}$ in Example 6, which is similar to the process for generating $H_{Plt-LD}$ shown in FIG. 5.

Figure 23:
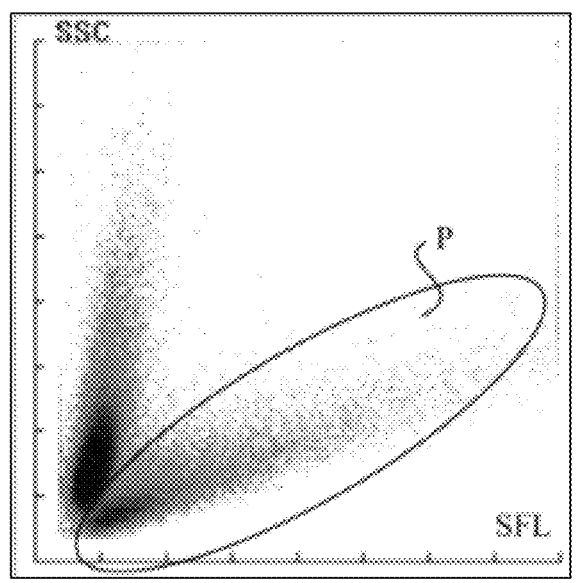
FIG. 23 shows a platelet distribution diagram corresponding to a SFL vs. SSC scattergram from a second suspension in one embodiment of the present disclosure.

It has been found that the platelet region can also be differentiated in the fluorescent (SFL) vs. side light scatter (SSC) scattergram, as shown in FIG. 23. Thus, fluorescent signals, forward angle light scatter signals and side light scatter signals are simultaneously measured when a sample passes through a nucleated red blood cell detection component. P region is differentiated in the fluorescent (SFL) vs. side light scatter (SSC) scattergram first, and then a derived platelet volume histogram $H_{Plt-ND}$ is obtained at least using the forward angle light scatter signals of each cell. The specific process is same as described above.

Figure 24:
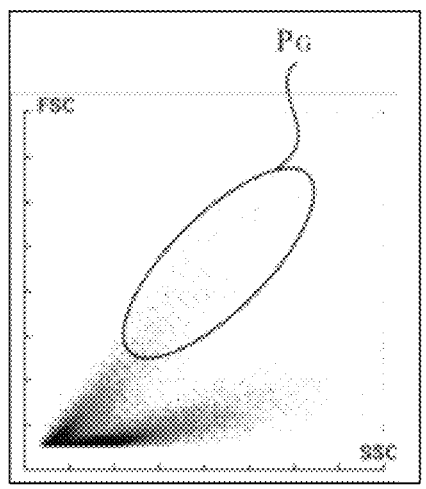
FIG. 24 shows a designated area PG within a platelet region in a FSC vs. SSC scattergram from a second suspension in one embodiment of the present disclosure.

Similarly, in Example 7, the platelet concentration of a sample may be determined using the process described above in reference to equations (13)-(15). FIG. 24 shows that the number of events appeared in the designated area $P_G$ within the platelet region in the FSC vs. SSC scattergram from the second suspension is normal. In this embodiment, such information from the second platelet distribution may be used together with the platelet valley/peak ratio $R_{v/p}$ in the platelet DC impedance histogram $H_{Plt-D}$ from the first suspension to determine the offset $F_{of}$ and the derived separation threshold $T_d$ using equations (13)-(15) and the offset criterion in the same manner as described above. In this case, in equations (14) and (15), N is the number of events in the designated area $P_G$ within the platelet region in the FSC vs. SSC scattergram from the second suspension. The derived separation threshold $T_d$ obtained is used to separate the platelets from the red blood cells in the platelet DC impedance histogram $H_{Plt-D}$ from the first suspension to obtain the platelet concentration as described below. Also, the designated area can be identified using the FSC vs. SSC scattergram, to determine whether the number of events is normal or not.

The embodiments described above provide accurate measurements of platelet concentration of blood samples, which are particularly effective in the presence of an interference to the impedance measurement methods, such as with blood samples containing fragmented red blood cells, microcytes, or large platelets. As such, the present methods have overcome the difficulties of existing impedance measurement methods and met a long felt need of accurate measurements of platelet concentration in in-vitro diagnostic analysis. Moreover, as discussed above some existing high end hematology analyzers use a separate optical measurement of platelets in addition to the conventional impedance measurement in order to differentiate interference substances and remove the effect of interferences. However, this substantially increases instrument complexity and manufacturing cost. In contrast, the instant methods can be implemented with existing complete blood count (CBC) and white blood cell differential measurements on various commercial hematology analyzers without increasing instrument cost. Therefore, the present methods are particularly advantageous in their broad applications in improving accuracy of platelet measurements on existing instruments in the field of in-vitro diagnostic industry.

The following examples are illustrative and are in no way to be interpreted as limiting the scope of the present disclosure, as defined in the claims. It will be understood that various modifications and changes can be made in accordance with the proceeding disclosure.

Example 1

Whole blood samples were measured on a commercial hematology analyzer BC-6800 (a product of Shenzhen Mindray Bio-Medical Electronics Co., Ltd., Shenzhen, China) and the data collected from measurements of the first and second suspensions were post analyzed using the method in one embodiment described above.

BC-6800 hematology analyzer has a CBC module and a differential module. The CBC module includes a mixing chamber configured to mix one aliquot of a blood sample with a diluent to form a first suspension and a DC impedance detector configured to measure DC impedance signals of the first suspension passing through an aperture in a flow path. The differential module includes another mixing chamber configured to mix another aliquot of the blood sample with a lytic agent and a fluorescent dye to form a second suspension, a red semiconductor laser with an emission wavelength of 640 nm as the light source which is configured with its light beam aimed at an orifice of an optical flow cell, and optical detectors enabling detection of forward angle light scatter signals from about 1° to about 10° and side scatter signals from about 65° to about 115° from the incident light beam, and fluorescent signals of the second suspension passing through the orifice of the optical flow cell.

In the CBC module, 44 of an anticoagulated whole blood sample was mixed with 1.5 mL of M-68DS diluent (a product of Shenzhen Mindray Bio-Medical Electronics Co., Ltd., Shenzhen, China) to form the first suspension. In the differential module, 20 μL of the same whole blood sample was mixed with 1 mL of M-68LD Lyse and 20 μL of M-68FD Dye (both are products of Shenzhen Mindray Bio-Medical Electronics Co., Ltd., Shenzhen, China) to lyse red blood cells and stain nucleated blood cells and to form the second suspension. The M-68LD Lyse was an aqueous solution containing a cationic surfactant, a nonionic surfactant, and an anionic compound for lysing red blood cells in a blood sample. The M-68FD Dye was an aqueous solution containing a cationic cyanine compound for staining nucleated blood cells in a blood sample.

The data collected from the measurement of DC impedance signals of the first suspension were post analyzed to generate a platelet DC impedance histogram $H_{Plt-D}$, as that illustrated in FIG. 1. The data collected from the measurements of forward angle light scatter signals and fluorescent signals of the second suspension were post analyzed to differentiate the platelet region (P) from the white blood cell region (W) in a SFL vs. FSC scattergram as illustrated in FIGS. 3A-3B. In this example, the derived platelet volume was calculated with equation (1) using the forward angle light scatter signals of platelets in the platelet region P. Then, a composite platelet histogram $H_{Plt-LD}$ was generated according to equation (3) described above. In this example, $k_{i1}$ and $k_{i2}$ in equation (3) were constants, wherein when $Vol_p(i) > 20$ fL, $k_{i1}=1$ and $k_{i2}=0$, and when $Vol_p(i) \leq 20$ fL, $k_{i1}=0$ and $k_{i2}=1$. The platelet concentration of a blood sample was determined according to the area under the curve in the composite platelet histogram $H_{Plt-LD}$.

25 whole blood samples were analyzed as described above, including five normal blood samples, ten abnormal blood samples which contained fragmented red blood cells or microcytes, and ten abnormal blood samples which contained large platelets. The presence of fragmented red blood cells, microcytes, or large platelets in these abnormal blood samples was confirmed by manual examination of blood smears under a microscope. These blood samples were further analyzed on a BriCyte E6 flow cytometer (a product of Shenzhen Mindray Bio-Medical Electronics Co., Ltd., Shenzhen, China) using the RBC/Platelet Ratio Method, a reference method as recommended by The International Council for Standardization in Hematology (ICSH) and the International Society of Laboratory Hematology (ISLH). Moreover, platelet concentrations of these blood samples reported on the BC-6800 hematology analyzer using a conventional DC impedance measurement method were also obtained for comparison.

FIG. 16 shows a correlation of the platelet concentrations of these blood samples obtained using the conventional DC impedance measurement method to the results obtained using the flow cytometry reference method. As shown, the platelet concentrations of these blood samples obtained using the conventional DC impedance measurement method correlated poorly with the reference method. The platelet concentrations of the abnormal blood samples containing fragmented red blood cells or microcytes were substantially higher than the results obtained by the flow cytometer reference method. On the other hand, the platelet concentrations of the abnormal blood samples containing large platelets were substantially lower than the results obtained by the reference method. The correlation coefficient ($R^2$) in the linear regression analysis of the results of these 25 blood samples was 0.8343.

FIG. 17 shows a correlation of the platelet concentrations of these blood samples obtained using the method described above associated with equation (3) to the results obtained using the flow cytometry reference method. As shown, the platelet concentrations obtained using the composite platelet histogram according to equation (3) correlated closely with the results from the flow cytometer reference method with a correlation coefficient ($R^2$) of 0.9940. The substantial errors occurred in the measurement by the conventional impedance method due to the presence of fragmented red blood cells, microcytes, or large platelets in the abnormal blood samples were effectively corrected using the composite platelet histogram $H_{Plt-LD}$ described above in this example.

Example 2

The data collected on the BC-6800 hematology analyzer from measurements of the first and second suspensions of the blood samples, as described above in Example 1, were further post analyzed to determine platelet concentrations of the blood samples using composite platelet histogram $H_{Plt-LDa}$ described above.

More specifically, same as in Example 1, the data collected from the measurements of DC impedance signals of the first suspension were post analyzed to generate a platelet DC impedance histogram $H_{Plt-D}$. The data collected from the measurements of forward angle light scatter signals and fluorescent signals of the second suspension were post analyzed to differentiate the platelet region (P) from the white blood cell region (W) in the SFL vs. FSC scattergram. A derived platelet volume histogram $H_{Plt-L}$ and derived platelet volumes were obtained using equation (1). Then, a composite platelet histogram $H_{Plt-LDa}$ was generated according to the criterion defined in equations (6) and (7) as described above. The platelet concentration of each blood sample was determined according to the area under the curve in the composite platelet histogram $H_{Plt-LDa}$.

The same 25 blood samples used in Example 1 were analyzed with the process described above in this example. FIG. 18 shows a correlation of the platelet concentrations of these blood samples obtained in this example to the results from the flow cytometry reference method obtained in Example 1. As shown, the platelet concentrations of these blood samples obtained using the method described in this example correlated closely with the results from the flow cytometer reference method, with a correlation coefficient ($R^2$) of 0.9739.

Example 3

The data collected on the BC-6800 hematology analyzer from measurements of the first and second suspensions of the blood samples, as described above in Example 1, were further post analyzed to determine platelet concentrations of blood samples using composite platelet histogram $H_{Plt-LDb}$ described above.

More specifically, the data collected from the measurement of DC impedance signals of the first suspension were post analyzed to generate a platelet DC impedance histogram $H_{Plt-D}$. The data collected from the measurements of forward angle light scatter signals and fluorescent signals of the second suspension were post analyzed to differentiate the platelet region P from the white blood cell region W in a SFL vs. FSC scattergram. In this example, a derived platelet volume histogram $H_{Plt-Lb}$ was generated with light scatter signals of platelets in the platelet region P using the curve fitting process defined by equation (8) as described above. Then, a composite platelet histogram $H_{Plt-LDb}$ was generated according to the criterion defined by equations (9) and (10) as described above. The platelet concentration of each blood sample was determined according to the area under the curve in the composite platelet histogram $H_{Plt-LDb}$.

The same 25 blood samples used in Example 1 were analyzed with the process described above in this example. FIG. 18 shows a correlation of the platelet concentrations of these blood samples obtained in this example to the results from the flow cytometry reference method obtained in Example 1. As shown, the platelet concentrations of these blood samples obtained using the method described in this example correlated closely with the results from the flow cytometry reference method, with a correlation coefficient ($R^2$) of 0.9681.

Example 4

The data collected on the BC-6800 hematology analyzer from measurements of the first and second suspensions of blood samples, as described above in Example 1, were further post analyzed to determine platelet concentrations of blood samples using equations (11) and (12) and the composing criterion described above.

More specifically, the data collected from the measurement of DC impedance signals of the first suspension were post analyzed to generate a platelet DC impedance histogram $H_{Plt-D}$. The data collected from the measurements of forward angle light scatter signals and fluorescent signals of the second suspension were post analyzed to differentiate the platelet region P from the white blood cell region W in a SFL vs. FSC scattergram. A derived platelet volume histogram $H_{Plt-L}$ and derived platelet volumes were obtained using equation (1). Then, the platelet concentration of each blood sample was calculated using equations (11) and (12) according to the composing criterion as described above.

Figure 19:
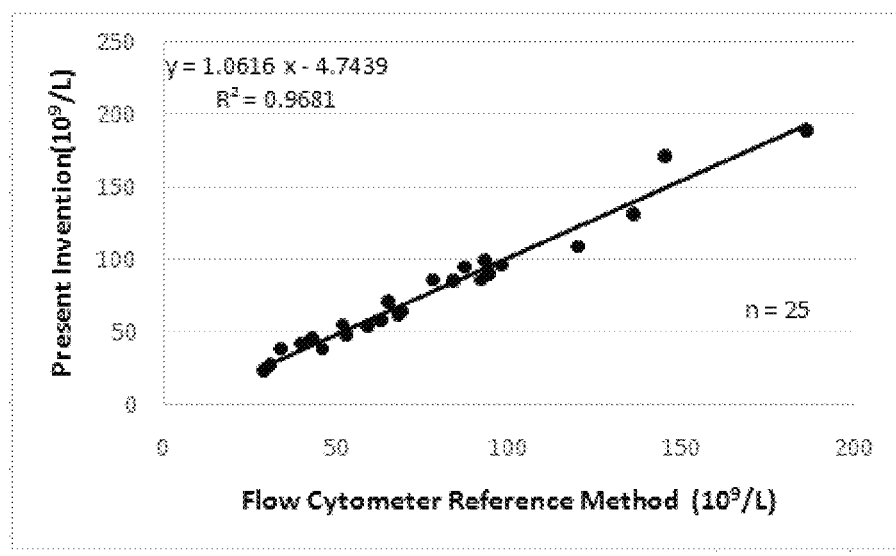
FIG. 19 shows a correlation of platelet concentrations of blood samples obtained using the method according to another embodiment of the present disclosure as described in Example 3 to platelet concentrations of these blood samples obtained using the flow cytometry reference method.

The same 25 blood samples used in Example 1 were analyzed with the process described above in this example. FIG. 19 shows a correlation of the platelet concentrations of these blood samples obtained in this example to the results from the flow cytometry reference method obtained in Example 1. As shown, the platelet concentrations of these blood samples obtained using the method described in this example correlated closely with the results from the flow cytometer reference method, with a correlation coefficient ($R^2$) of 0.9797.

Example 5

The data collected on the BC-6800 hematology analyzer from measurements of the first and second suspensions of blood samples, as described above in Example 1, were further post analyzed using the method in a further embodiment described above.

More specifically, same as described in Example 1, the data collected from the measurement of DC impedance signals of the first suspension were post analyzed to generate a platelet DC impedance histogram $H_{Plt-D}$, as those illustrated in FIGS. 9B and 10B, and to determine the platelet valley/peak ratio $R_{v/p}$ in the histogram. The data collected from the measurements of forward angle light scatter signals and fluorescent signals of the second suspension were post analyzed to differentiate the platelet region P from the white blood cell region W in a SFL vs. FSC scattergram, and to determine the number of events N in the designated area $P_G$. Then, a derived separation threshold $T_d$ was determined according to equations (13)-(15) and the offset criterion described above. The obtained derived separation threshold $T_d$ was used then to separate the platelets from the red blood cells in the platelet DC impedance histogram $H_{Plt-D}$, as illustrated in FIGS. 9C and 10C, and the platelet concentration of each blood sample was calculated according to the area under the curve for the platelet population as defined by the derived separation threshold $T_d$ in the platelet DC impedance histogram.

Figure 20:
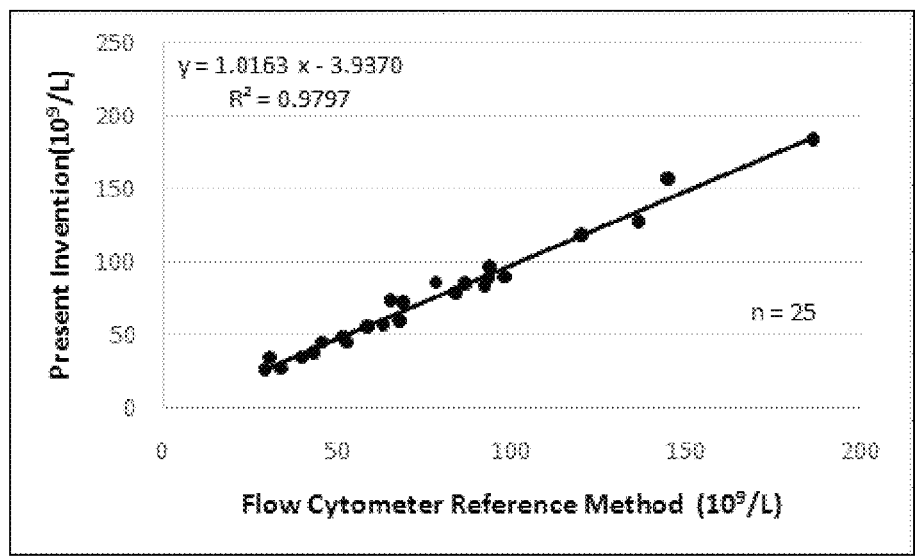
FIG. 20 shows a correlation of platelet concentrations of blood samples obtained using the method according to yet a further embodiment of the present disclosure as described in Example 4 to platelet concentrations of these blood samples obtained using the flow cytometry reference method.

The same 25 blood samples used in Example 1 were analyzed with the process described above in this example. FIG. 20 shows a correlation of the platelet concentrations of these blood samples obtained in this example to the results from the flow cytometry reference method obtained in Example 1. As shown, the platelet concentrations of these blood samples obtained using the method described in this example correlated closely with the results from the flow cytometer reference method, with a correlation coefficient ($R^2$) of 0.9937. Same as in other examples above, the substantial errors occurred in the measurement by the conventional impedance method due to the presence of fragmented red blood cells, microcytes, or large platelets in the abnormal blood samples were effectively corrected using the method in this example.

Example 6

A whole blood sample containing nucleated red blood cells was measured on a commercial hematology analyzer BC-6800 (a product of Shenzhen Mindray Bio-Medical Electronics Co., Ltd., Shenzhen, China) and the data collected from measurements of the first and second suspensions were post analyzed using the method in one embodiment described above.

BC-6800 hematology analyzer has a CBC module and a differential module. The CBC module includes a mixing chamber configured to mix one aliquot of a blood sample with a diluent to form a first suspension and a DC impedance detector configured to measure DC impedance signals of the first suspension passing through an aperture in a flow path. The differential module is a differential module for nucleated red blood cell and includes another mixing chamber configured to mix another aliquot of the blood sample with a lytic agent and a fluorescent dye to form a second suspension, a red semiconductor laser with an emission wavelength of 640 nm as the light source which is configured with its light beam aimed at an orifice of an optical flow cell, and optical detectors enabling detection of forward angle light scatter signals from about 1° to about 10° and side scatter signals from about 65° to about 115° from the incident light beam, and fluorescent signals of the second suspension passing through the orifice of the optical flow cell.

In the CBC module, 4 μL of an anticoagulated whole blood sample was mixed with 1.5 mL of M-68DS diluent (a product of Shenzhen Mindray Bio-Medical Electronics Co., Ltd., Shenzhen, China) to form the first suspension. In the differential module, 20 μL of the same whole blood sample was mixed with 1 mL of M-68LN Lyse and 20 μL of M-68FN Dye (both are products of Shenzhen Mindray Bio-Medical Electronics Co., Ltd., Shenzhen, China) to lyse red blood cells and stain nucleated blood cells and to form the second suspension. The M-68LN Lyse was an aqueous solution containing a cationic surfactant and an anionic compound for lysing red blood cells in a blood sample. The M-68FN Dye was an aqueous solution containing a cationic cyanine compound for staining nucleated blood cells in a blood sample.

The data collected from the measurement of DC impedance signals of the first suspension were post analyzed to generate a platelet DC impedance histogram $H_{Plt-D}$, as that illustrated in FIG. 1. The data collected from the measurements of forward angle light scatter signals and fluorescent signals of the second suspension were post analyzed to differentiate the platelet region P from the white blood cell region W in a SFL vs. FSC scattergram as illustrated in FIG. 22. In this example, derived platelet volumes were calculated using equation (1) based on forward angle light scatter signals of platelets in the platelet region P. A derived platelet volume histogram $H_{Plt-N}$ as illustrated in FIG. 22, was generated. Then, a composite platelet histogram $H_{Plt-LD}$ was generated according to equation (3) described above. In this example, $k_{i1}$ and $k_{i2}$ in equation (3) were constants, wherein when $Vol_p(i) > 20$ fL, $k_{i1}=1$ and $k_{i2}=0$, and when $Vol_p(i)$ 20 fL, $k_{i1}=0$ and $k_{i2}=1$. The platelet concentration of a blood sample was determined according to the area under the curve in the composite platelet histogram $H_{Plt-LD}$.

Figure 26:
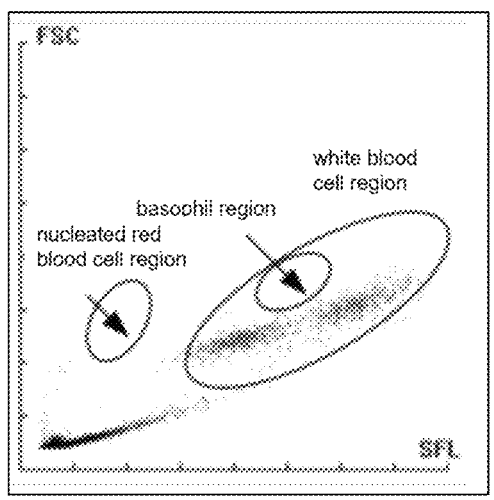
FIG. 26 shows a FSC vs. SFL scattergram from a second suspension of a blood sample illustrating identification of nucleated red blood cells in one embodiment of the present disclosure as described in Example 6.

As shown in FIG. 26, nucleated red blood cells and white blood cells were identified and counted using the light scatter signals and fluorescent signals of the second suspension of the blood sample.

The blood sample was confirmed to contain fragmented red blood cells by manual examination of blood smears under a microscope. The reference value obtained by the flow cytometry reference method was $86 \times 10^9$/L, the platelet count result obtained by the impedance method was $110 \times 10^9$/L and the platelet count result obtained by the present disclosure was $91 \times 10^9$/L, which was closer to the reference value.

Example 7

A whole blood sample containing nucleated red blood cells was measured on a commercial hematology analyzer BC-6800 (a product of Shenzhen Mindray Bio-Medical Electronics Co., Ltd., Shenzhen, China) and the data collected from measurements of the first and second suspensions were post analyzed using the method in one embodiment described above.

BC-6800 hematology analyzer has a CBC module and a differential module. The CBC module includes a mixing chamber configured to mix one aliquot of a blood sample with a diluent to form a first suspension and a DC impedance detector configured to measure DC impedance signals of the first suspension passing through an aperture in a flow path. The differential module is a differential module for nucleated red blood cell and includes another mixing chamber configured to mix another aliquot of the blood sample with a lytic agent and a fluorescent dye to form a second suspension, a red semiconductor laser with an emission wavelength of 640 nm as the light source which is configured with its light beam aimed at an orifice of an optical flow cell, and optical detectors enabling detection of forward angle light scatter signals from about 1° to about 10° and side scatter signals from about 65° to about 115° from the incident light beam, and fluorescent signals of the second suspension passing through the orifice of the optical flow cell.

In the CBC module, 4 μL of an anticoagulated whole blood sample was mixed with 1.5 mL of M-68DS diluent (a product of Shenzhen Mindray Bio-Medical Electronics Co., Ltd., Shenzhen, China) to form the first suspension. In the differential module, 20 μL of the same whole blood sample was mixed with 1 mL of M-68LN Lyse and 20 μL of M-68FN Dye (both are products of Shenzhen Mindray Bio-Medical Electronics Co., Ltd., Shenzhen, China) to lyse red blood cells and stain nucleated blood cells and to form the second suspension. The M-68LN Lyse was an aqueous solution containing a cationic surfactant and an anionic compound for lysing red blood cells in a blood sample. The M-68FN Dye was an aqueous solution containing a cationic cyanine compound for staining nucleated blood cells in a blood sample.

Figure 25A:
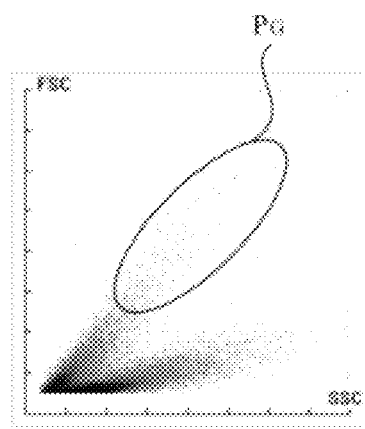
FIGS. 25A-25C further illustrate a process of determining a platelet concentration in a blood sample using a derived separation threshold Td.
Figure 25B:
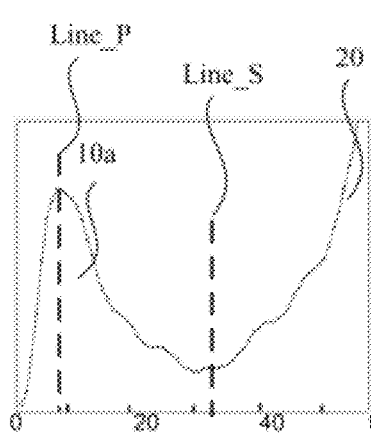
Figure 25C:
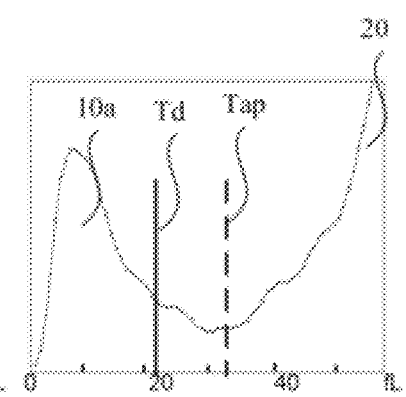

The data collected from the measurement of DC impedance signals of the first suspension were post analyzed to generate a platelet DC impedance histogram $H_{Plt-D}$, as that illustrated in FIG. 25B, and to determine the platelet valley/peak ratio $R_{v/p}$ in the histogram. The data collected from the measurements of forward angle light scatter signals and fluorescent signals of the second suspension were post analyzed to differentiate the platelet region P from the white blood cell region W in a SFL vs. FSC scattergram, and to determine the number of events N in the designated area $P_G$. Then, a derived separation threshold $T_d$ was determined according to equations (13)-(15) and the offset criterion described above. The obtained derived separation threshold $T_d$ was used then to separate the platelets from the red blood cells in the platelet DC impedance histogram $H_{Plt-D}$. In this example, the number of events N in the designated area $P_G$ was normal, and the derived separation threshold $T_d$ was left shifted from the apparent separation threshold Tap, as shown in FIG. 25C, and the platelet concentration of the blood sample was calculated according to the area under the curve for the platelet population as defined by the derived separation threshold $T_d$ in the platelet DC impedance histogram.

The blood sample was confirmed to contain fragmented red blood cells by manual examination of blood smears under a microscope. The reference value obtained by the flow cytometry reference method was $86 \times 10^9$/L, the platelet count result obtained by the impedance method was $110 \times 10^9$/L, and the platelet count result obtained by the present disclosure was $95 \times 10^9$/L, which was closer to the reference value.

While the present disclosure has been described in detail and pictorially shown in the accompanying drawings, these should not be construed as limitations on the scope of the present disclosure, but rather as an exemplification of preferred embodiments thereof. It will be apparent, however, that various modifications and changes can be made within the scope of this disclosure as described in the above specification and defined in the appended claims and their legal equivalents. All patents and other publications cited herein are expressly incorporated by reference.

What is claimed is:

1. A method for analyzing a blood sample, comprising:
   acquiring DC impedance signals of a first suspension from the blood sample;
   acquiring at least two types of optical signals of a second suspension from the blood sample, wherein the at least two types of optical signals comprise forward angle light scatter signals and first optical signals for providing cellular content information;
   acquiring a first platelet distribution using the DC impedance signals;
   acquiring a second platelet distribution using the at least two types of optical signals; and
   acquiring a third platelet distribution using the first platelet distribution and the second platelet distribution;
   wherein the first suspension is formed by mixing a first aliquot of the blood sample with a diluent, and the second suspension is formed by mixing a second aliquot of the blood sample with a treatment reagent, which comprises a lytic agent to lyse red blood cells in the second aliquot of the blood sample.

2. The method for analyzing a blood sample of claim 1, further comprising outputting at least one of the first platelet distribution, the second platelet distribution and the third platelet distribution.

3. The method for analyzing a blood sample of claim 1, wherein said acquiring the second platelet distribution comprises:
   obtaining a scattergram of the second suspension using the at least two types of optical signals; and
   differentiating platelets from white blood cells and/or nucleated red blood cells in the scattergram to obtain a platelet region.

4. The method for analyzing a blood sample of claim 3, wherein said acquiring the second platelet distribution further comprises:
   acquiring a derived platelet volume histogram of the blood sample using the forward angle light scatter signals of the platelet region.

5. The method for analyzing a blood sample of claim 4, wherein the first platelet distribution comprises a platelet DC impedance histogram of the blood sample; and
   said acquiring the third platelet distribution comprises acquiring a composite platelet histogram using the platelet DC impedance histogram and the derived platelet volume histogram based on a preset criterion.

6. The method for analyzing a blood sample of claim 5, wherein said acquiring the third platelet distribution further comprises acquiring platelet analysis data of the blood sample using the composite platelet histogram, wherein the platelet analysis data comprises at least one of a platelet count, a mean platelet volume and a platelet volume distribution width.

7. The method for analyzing a blood sample of claim 3, wherein said acquiring the second platelet distribution further comprises acquiring a number of events in a designated area within the platelet region.

8. The method for analyzing a blood sample of claim 7, wherein the first platelet distribution comprises a platelet DC impedance histogram of the blood sample; and said acquiring the third platelet distribution comprises determining a platelet valley/peak ratio in the platelet DC impedance histogram, determining a derived separation threshold in the platelet DC impedance histogram using the platelet valley/peak ratio and the number of events in the designated area, and acquiring platelet analysis data of the blood sample, wherein the platelet analysis data comprises at least one of a platelet count, a mean platelet volume and a platelet volume distribution width.

9. The method for analyzing a blood sample of claim 8, further comprising displaying at least one of the platelet region, the designated area, the platelet valley/peak ratio, the platelet DC impedance histogram including the derived separation threshold, and the platelet analysis data.

10. The method for analyzing a blood sample of claim 1, wherein the first optical signals are selected from at least one type of side light scatter signals and medium angle light scatter signals.

11. The method of analyzing a blood sample of claim 10, further comprising differentiating white blood cells of the blood sample into white blood cell subpopulations using the at least two types of optical signals of the second suspension; and based on the at least two types of optical signals of the second suspension, differentiating white blood cells of the blood sample into monocytes, lymphocytes, neutrophils and eosinophils or into basophils; or enumerating the white blood cells of the blood sample in the second suspension; or identifying nucleated red blood cells or immature white blood cells in the second suspension.

12. A hematology system, comprising:

a first module comprising a first mixing chamber configured to mix a first aliquot of a blood sample with a diluent to form a first suspension, and a DC impedance detector equipped with an aperture in a flow path connected with the first mixing chamber, the DC impedance detector configured to measure DC impedance signals of the first suspension passing through the aperture;

a second module comprising a second mixing chamber configured to mix a second aliquot of the blood sample with a treatment reagent to form a second suspension, a light source configured with a light beam aimed at an orifice of an optical flow cell in a flow path connected with the second mixing chamber, and one or more optical detectors equipped with the optical flow cell and configured to measure at least two types of optical signals of the second suspension passing through the optical flow cell, wherein the treatment reagent comprises lytic agent to lyse red blood cells in the second aliquot of the blood sample, and the at least two types of optical signals comprise forward angle light scatter signals and first optical signals for providing cellular content information; and a data processing module operably connecting with the DC impedance detector in the first module and the one or more optical detectors in the second module, respectively, the data processing module comprising a processor and a non-transitory computer readable medium programmed with a computer application program that, when executed by the processor, causes the processor to acquire a first platelet distribution using the DC impedance signals, to acquire a second platelet distribution using the at least two types of optical signals, and to acquire a third platelet distribution using the first platelet distribution and the second platelet distribution.

13. The hematology system of claim 12, wherein to acquire the second platelet distribution, the data processing module is further configured to obtain a scattergram of the second suspension using the at least two types of optical signals and differentiates platelets from white blood cells in the scattergram to obtain a platelet region.

14. The hematology system of claim 13, wherein to acquire the second platelet distribution, the data processing module is further configured to acquire a derived platelet volume histogram of the blood sample using the at least two types of optical signals of the platelet region.

15. The hematology system of claim 14, wherein the first platelet distribution comprises a platelet DC impedance histogram; and wherein to acquire the third platelet distribution, the data processing module is further configured to acquire a composite platelet histogram using the platelet DC impedance histogram and the derived platelet volume histogram based on a preset criterion.

16. The hematology system of claim 15, wherein to acquire the third platelet distribution, the data processing module is further configured to acquire platelet analysis data of the blood sample using the composite platelet histogram, wherein the platelet analysis data comprises at least one of a platelet count, a mean platelet volume and a platelet volume distribution width.

17. The hematology system of claim 16, wherein to acquire the second platelet distribution, the data processing module is configured to acquire a number of events in a designated area within the platelet region.

18. The hematology system of claim 17, wherein the first platelet distribution comprises a platelet DC impedance histogram of the blood sample; and wherein to acquire the third platelet distribution, the data processing module is further configured to determine a platelet valley/peak ratio in the platelet DC impedance histogram, determine a derived separation threshold in the platelet DC impedance histogram using the platelet valley/peak ratio and the number of events in the designated area, and acquire platelet analysis data of the blood sample, wherein the platelet analysis data comprises at least one of a platelet count, a mean platelet volume and a platelet volume distribution width.

19. The hematology system of claim 18, further comprising a user interface operably connecting with the data processing module and configured to display at least one of the platelet region, the designated area, the platelet valley/peak ratio, the platelet DC impedance histogram including the derived separation threshold and the platelet analysis data.

20. The hematology system of claim 12, wherein the first optical signals are selected from at least one type of side light scatter signals and medium angle light scatter signals.

21. The hematology system of claim 20, wherein the data processing module is further configured to:

differentiate white blood cells of the blood sample into white blood cell subpopulations comprising monocytes, lymphocytes, neutrophils and eosinophils, or into basophils, using the at least two types of optical signals of the second suspension; and enumerate the white blood cells of the blood sample in the second suspension; or identify nucleated red blood cells or immature white blood cells in the second suspension.

\* \* \* \* \*